(12) United States Patent
Boamah et al.

(10) Patent No.: US 11,375,912 B2
(45) Date of Patent: Jul. 5, 2022

(54) LIQUID FLOW INDUCED POWER GENERATION USING NANOSCALE METAL LAYERS

(71) Applicant: Northwestern University, Evanston, IL (US)

(72) Inventors: Mavis D. Boamah, Evanston, IL (US); Franz M. Geiger, Evanston, IL (US)

(73) Assignee: Northwestern University, Evanston, IL (US)

( * ) Notice: Subject to any disclaimer, the term of this patent is extended or adjusted under 35 U.S.C. 154(b) by 189 days.

(21) Appl. No.: 16/941,264

(22) Filed: Jul. 28, 2020

(65) Prior Publication Data

US 2020/0358374 A1 Nov. 12, 2020

Related U.S. Application Data

(63) Continuation of application No. PCT/US2019/051412, filed on Sep. 17, 2019.

(60) Provisional application No. 62/879,923, filed on Jul. 29, 2019, provisional application No. 62/772,319, (Continued)

(51) Int. Cl.
*H02N 11/00* (2006.01)
*A61B 5/026* (2006.01)
*H02N 1/08* (2006.01)

(52) U.S. Cl.
CPC ............... *A61B 5/026* (2013.01); *H02N 1/08* (2013.01); *H02N 11/002* (2013.01)

(58) Field of Classification Search
CPC ........ A61B 5/206; H02N 11/002; H02N 1/08; H02N 3/00; Y02E 10/50; G01F 1/56; G01F 1/86; B82B 1/00; B82B 1/001; B82B 1/008; C23C 14/08; C23C 14/081; C23C 14/082; C23C 14/083; C23C 14/085; C23C 14/086; C23C 14/087; C23C 14/088
See application file for complete search history.

(56) References Cited

U.S. PATENT DOCUMENTS

| 6,008,625 | A | 12/1999 | Gan et al. |
| 6,718,834 | B1 * | 4/2004 | Sood ........................ G01P 5/08 |
| | | | 977/953 |
| 6,791,205 | B2 | 9/2004 | Woodbridge |
| (Continued) | | | |

FOREIGN PATENT DOCUMENTS

| GB | 2572330 | * | 2/2020 | ............... H02N 2/18 |
| KR | 101419742 | * | 7/2014 | ............... H02N 3/00 |
| WO | WO 2020/117351 A2 | | 6/2020 | |

OTHER PUBLICATIONS

Z. Zhou, S. Bao, J. Shen and R. Xu, "Bubble-Induced Voltage Generation on Graphene Layer," 2020 IEEE Sensors, 2020, pp. 1-4, doi: 10.1109/SENSORS47125.2020.9278731. (Year: 2020).*

(Continued)

*Primary Examiner* — Burton S Mullins

(74) *Attorney, Agent, or Firm* — Bell & Manning, LLC

(57) ABSTRACT

Energy harvesting devices and methods for converting the mechanical energy of a flowing ionic solution, such as rainwater or seawater, into electric energy are provided. The energy harvesting devices include an electric current generating device that includes a metal layer and an amphoteric metal oxide film disposed over a surface of the metal layer.

(Continued)

By moving an electric double layer across the surface of the amphoteric metal oxide film, an electric current is generated in the metal layer.

26 Claims, 36 Drawing Sheets

Related U.S. Application Data filed on Nov. 28, 2018, provisional application No. 62/732,822, filed on Sep. 18, 2018.

(56) References Cited

U.S. PATENT DOCUMENTS

| | | | |
|---|---|---|---|
| 7,932,618 B2 | 4/2011 | Baarman | |
| 7,982,371 B1* | 7/2011 | Anand | F03G 7/005 310/330 |
| 8,170,673 B2* | 5/2012 | Axelrod | H01M 10/46 607/34 |
| 8,381,598 B2* | 2/2013 | Achard | B01L 3/502715 73/861.12 |
| 8,778,563 B2* | 7/2014 | Wang | H01M 8/0289 429/523 |
| 9,013,092 B2* | 4/2015 | Mahapatra | B82Y 15/00 310/339 |
| 9,368,283 B2 | 6/2016 | Wright et al. | |
| 9,559,617 B2* | 1/2017 | Landa | B28B 11/24 |
| 9,738,966 B2 | 8/2017 | Geiger et al. | |
| 9,771,650 B2* | 9/2017 | Fischer | C23C 14/5873 |
| 9,786,718 B1* | 10/2017 | Boyd | H01J 45/00 |
| 9,981,054 B2 | 5/2018 | Johnson | |
| 10,270,370 B2* | 4/2019 | Kim | H02N 1/08 |
| 10,439,517 B2* | 10/2019 | Wang | H02N 1/04 |
| 2010/0171394 A1 | 7/2010 | Glenn et al. | |
| 2013/0026409 A1 | 1/2013 | Baker et al. | |
| 2014/0016501 A1 | 1/2014 | Kamath et al. | |
| 2015/0124311 A1 | 5/2015 | Parrot | |
| 2016/0068944 A1 | 3/2016 | Geiger et al. | |
| 2016/0174900 A1 | 6/2016 | Zdeblick et al. | |
| 2016/0324435 A1 | 11/2016 | Kuzum et al. | |
| 2018/0183038 A1 | 6/2018 | Yao et al. | |
| 2020/0298238 A1* | 9/2020 | Kim | B01L 3/502792 |
| 2022/0038032 A1 | 2/2022 | Boamah et al. | |

OTHER PUBLICATIONS

Boamah et al., "Dendritic Oxide Growth in Zero-Valent Iron Nanofilms Revealed by Atom Probe," Department of Chemistry, Northwestern University, Evanston, IL 60208, pp. 1-33.

Paul E. Ohno et al., « Phase-referenced nonlinear spectroscopy of the α-quartz/water interface, Nature Communications, vol. 7, Published Dec. 13, 2016, DOI: 10.1038/ncomms13587, pp. 1-5.

The International Search Report and the Written Opinion issued in International Patent Application No. PCT/US19/51412 dated Jun. 8, 2020, pp. 1-8.

Boamah et al., "Energy conversion via metal nanolayers," Proceedings of the National Academy of Sciences, vol. 116, No. 33, Aug. 13, 2019, pp. 1620-16215.

Kim et al., "Ion specificity on electric energy generated by flowing water droplet," Angewandte Chemie International Edition, vol. 57, No. 8, Feb. 19, 2018, pp. 2091-2095.

Li et al., "Hydroelectric generator from transparent flexible zinc oxide nanofilms," Nano Energy, vol. 32, 2017, pp. 125-129.

Park et al., "Identification of droplet-flow-induced electric energy on electro-lyte-insulator-semiconductor structure," Journal of the American Chemical Society, vol. 139, No. 32, Aug. 16, 2017, pp. 10968-10971.

The International Search Report and the Written Opinion issued in International Patent Application No. PCT/US19/51421 dated Jul. 9, 2020, pp. 1-14.

Wikipedia."Vanadium(V) Oxide." Wikipedia, Wikimedia Foundation (May 9, 2018).

Jun Yin et al., "Generating electricity by moving a droplet of ionic liquid along graphene," Nature Nanotechnology, vol. 9, May 2014, pp. 377-383.

Shanshan Yang et al., "Mechanism of Electric Power Generation from Ionic Droplet Motion on Polymer Supported Graphene," *Institute of Nanoscience*, Nanjing University of Aeronautics and Astronautics, Nanjing 210016, China. Department of Physics, University of California, Berkeley, CA 94720, United States, pp. 1-21.

D. H. Huynh et al., "Environmentally friendly power generator based on moving liquid dielectric and double layer effect," ScieSB0tific reports, vol. 6, 26708, pp. 1-20. DOI: 10.1038/srep26708.

The International Search Report and the Written Opinion dated Dec. 23, 2021 for international patent application No. PCT/US21/71007; pp. 1-12.

* cited by examiner

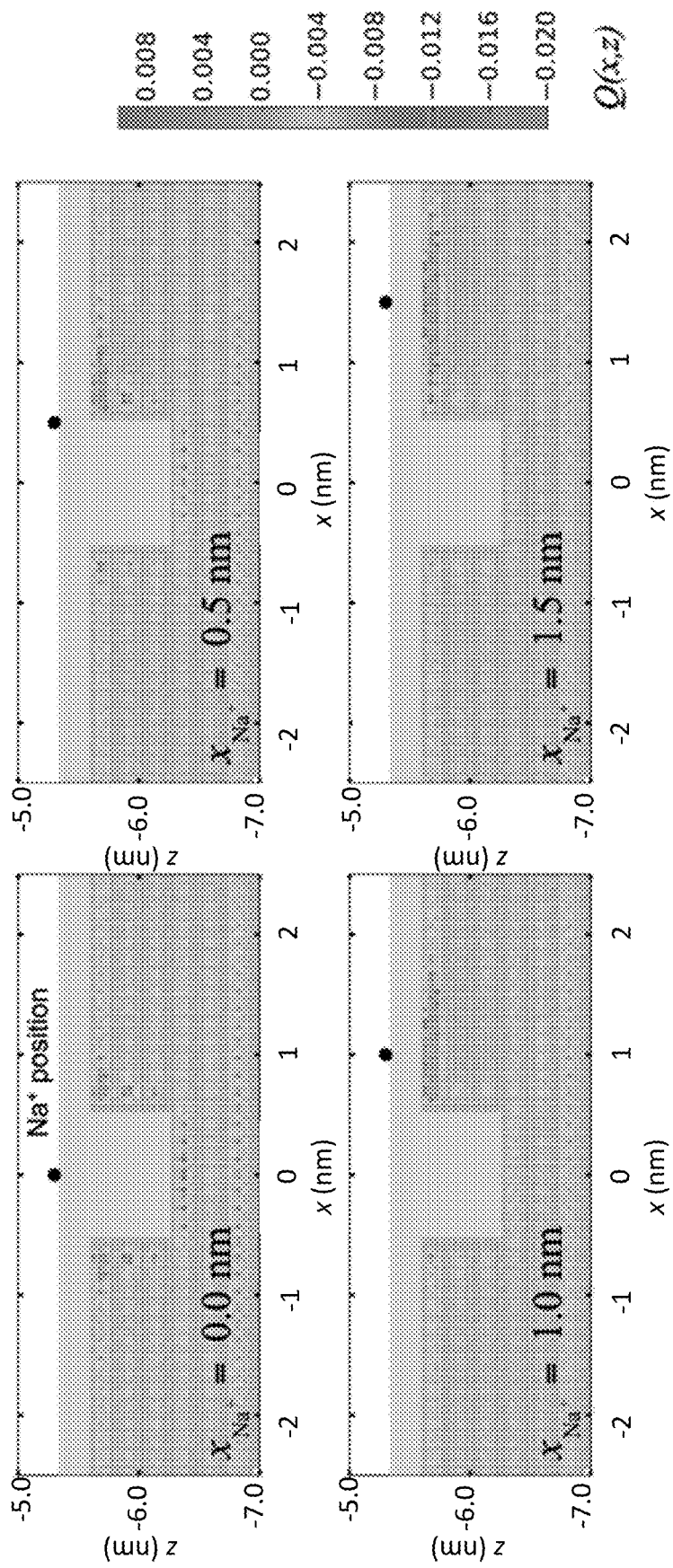

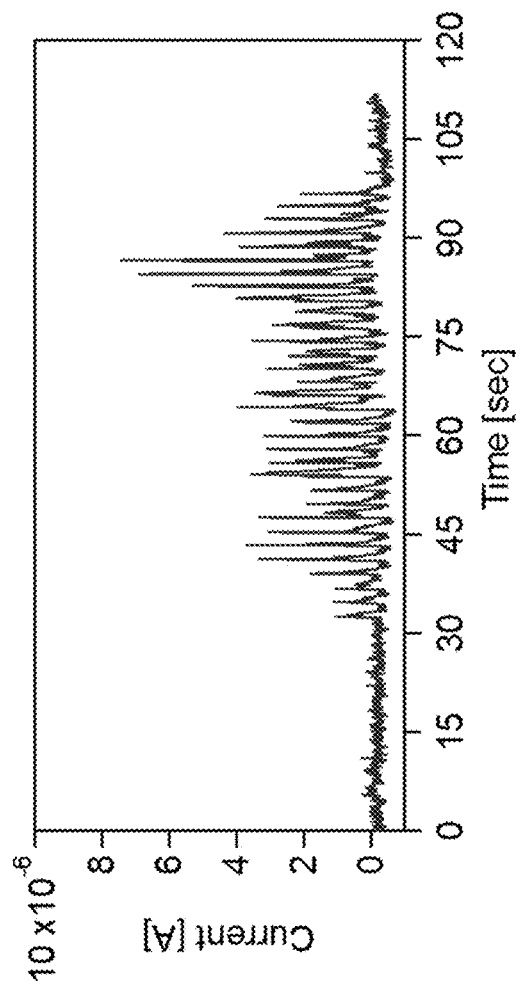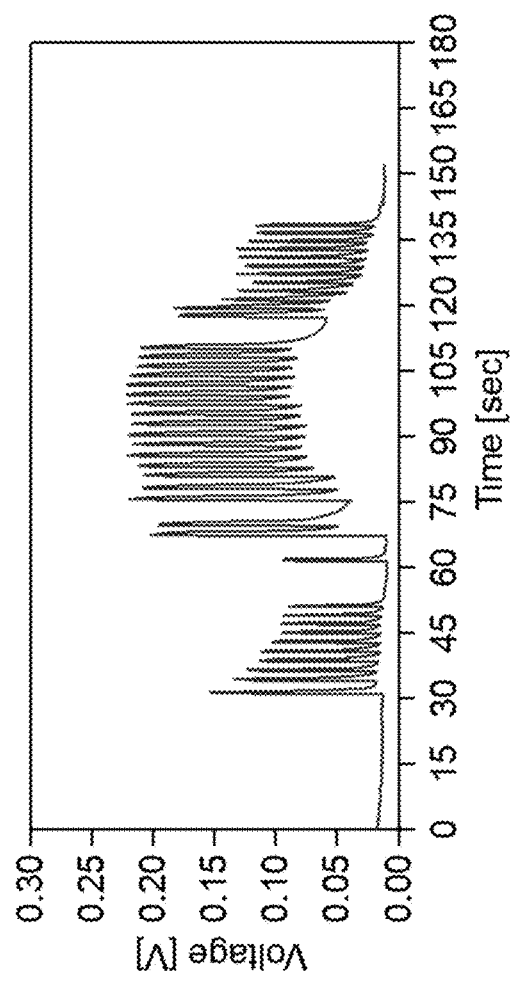
FIG. 21A
FIG. 21B

LIQUID FLOW INDUCED POWER GENERATION USING NANOSCALE METAL LAYERS

CROSS-REFERENCE TO RELATED APPLICATIONS

The present application is a continuation-in-part of PCT application number PCT/US2019/051412 that was filed on Sep. 17, 2019, the entire contents of which are incorporated herein by reference. PCT application number PCT/US2019/051412 claims priority to U.S. provisional patent application No. 62/732,822 that was filed Sep. 18, 2018, U.S. provisional patent application No. 62/772,319 that was filed Nov. 28, 2018, and U.S. provisional patent application No. 62/879,923 that was filed Jul. 29, 2019, the entire contents of which are incorporated herein by reference.

REFERENCE TO GOVERNMENT RIGHTS

This invention was made with government support under grant number 0950433 awarded by the National Science Foundation and grant number W911NF-19-1-0361awarded by the DOD/DARPA The government has certain rights in the invention.

BACKGROUND

Current methods and devices for achieving kinetic/gravitational to electrical energy conversion use conducting or semi-conducting layered materials in contact with moving aqueous droplets or brushes. The most successful approaches, based on carbon nanotubes, graphene, and dielectric-semiconductor architectures, are promising as they show efficiencies of around 30 percent. However, even the most successful approaches pose challenges related to fabrication, scaling, and long-term stability during operation in the field.

SUMMARY

Energy harvesting devices and methods of using the devices to convert the mechanical energy of a flowing ionic solution into electric energy are provided. Also provided are flow sensors and methods for using the flow sensors to monitor the flow of an ionic solution. The devices utilize the flowing ionic solution to move an electrical double layer across a metal layer, thereby generating a current in the metal layer.

One embodiment of a liquid flow-based device includes: a metal layer comprising a metal; an amphoteric metal oxide film adjacent to the metal layer at an interface, the amphoteric metal oxide film having a surface disposed opposite the interface, wherein the metal layer has a thickness that facilitates charge carrier motion parallel to the interface; and at least one of: an electronic device connected laterally across the metal layer. The electronic device may be: a device that consumes electrical power that is configured to be powered by a current running parallel to the interface; an energy storage device that is configured to be charged by a current running parallel to the interface; a voltage measuring device configured to measure a voltage across the metal layer; and/or a current measuring device that is configured to measure a current running parallel to the interface.

One embodiment of a method of harvesting energy using a device of the type described herein includes the steps of: exposing the surface of the amphoteric metal oxide film to an intermittent flow of an ionic solution or to a flow of an ionic solution having a temporally varying ionic conductivity, wherein the intermittent flow or the temporally varying ionic conductivity generates a current in the metal layer; and powering the electronic device or charging the energy storage device with the generated current.

One embodiment of a method of monitoring the flow of an ionic solution using a device of the type described herein includes the steps of: exposing the surface of the amphoteric metal oxide film to an intermittent flow of an ionic solution or to a flow of an ionic solution having a temporally varying ionic conductivity, wherein the intermittent flow or the temporally varying ionic conductivity generates a current in the metal layer; and measuring the voltage across the metal layer as the ionic solution passes over the surface of the amphoteric metal oxide film.

BRIEF DESCRIPTION OF THE DRAWINGS

Illustrative embodiments of the invention will hereafter be described with reference to the accompanying drawings, wherein like numerals denote like elements.

FIG. 1A depicts one embodiment of an energy harvesting device. FIG. 1B is a cartoon representation of the use of stacked nanofilms inside a pipe for electrical power extraction from temporally varying ionic solution flows, such as oceanic tides, or flows of alternating salinity in estuaries and fjords.

FIG. 2A depicts current induced in a 10 nm Fe:FeOx nanolayer ($3\times1$ in$^2$) when flowing deionized (DI) water at pH 5.8 for 20 sec (black segment), followed by 20 sec flow of 1 M NaCl held at pH 7 (grey segment), and six subsequent replicates, all at a constant flow rate of 20 mL min$^{-1}$. FIG. 2B depicts the same as in FIG. 2A but measured using a $3\times9$ in$^2$Fe:FeOx nanolayer of 10 nm thickness at a flow rate of 100 mL min$^{-1}$ and 2 min between switching salt concentration. FIG. 2C depicts the same as in FIG. 2B but measured at a flow rate of 35 mL min$^{-1}$ and constant 0.6 M salt concentration while reversing the flow direction every 2 min, marked by the vertical grey lines.

FIG. 4A depicts voltage induced in a 50 nm (black trace) and 10 nm (gray trace) thin iron nanofilm (data offset for clarity); 15 μL drops at a drop rate of 0.5 mL min$^{-1}$. FIG. 4B depicts voltage induced in a 2 mm thick iron plate, commercial aluminum foil (data offset for clarity), and aluminum film inside a snack bag (data offset for clarity); 15 μL drops at a drop rate of 0.5 mL min$^{-1}$.

FIG. 5A depicts open-circuit voltage (OCV) measured perpendicular to the drop motion while dropping a 0.6 M aqueous salt solution (pH 5.8) over a 5 nm thin iron nanofilm at a drop rate=0.5 mL/min and (FIG. 5B) when reversing the polarity of the probes.

FIG. 8A depicts induced current in a 10 nm iron nanofilm using aqueous solutions of alternating salinity (0.1M and DI water, 25 mL min$^{-1}$, 20 sec flow per salinity)

over ~1 hour. FIG. 8B depicts induced current before, during, and after low-to-high salinity transition in a flow cell.

FIG. 9A depicts average current densities measured as a function of aqueous flow velocity using 10 nm thin nanolayers of Fe:FeOx, Ni:NiOx, V:VOx, Al:AlOx, and Cr:CrOx while alternating DI water (pH=5.8) and 0.6 M NaCl solution (pH ~7) segments every 20 sec, and current density obtained for 30 μL drops falling with a 0.1 to 0.2 cm$^2$ contact area onto a 10 nm thick Fe:FeOx nanolayer deposited onto a 1×3 in$^2$ glass substrate while alternating the drop salinity between DI water and 0.6 M at a drop rate of 2 mL min$^{-1}$ and an incident angle of ~160° (vertical bar). Error bars on point estimates shown are for 1 standard deviation (σ) from n=7 and 8 replicate measurements per flow rate. FIG. 9B depicts the same as FIG. 9A but for a 10 nm Fe:FeOx nanolayer as a function of aqueous flow velocity and for a 10 nm thin nanolayer of pure FeOx (no metal present) and a 10 nm thin nanolayer of pure TiOx. FIG. 9C depicts current density recorded for Fe:FeOx nanolayers varying in total thickness obtained with a flow velocity of 0.74 cm s$^{-1}$ while alternating DI water and 0.6 M NaCl solution segments every 20 sec. FIG. 9D depicts current density obtained for a 30 nm Fe:FeOx nanolayer without and with a 5 nm Cr:CrOx nanolayer on top of it obtained with a flow velocity of 1.15 cm s$^{-1}$, and for a 30 nm nanolayer of pure FeOx (no metal present) obtained with a flow velocity of 1 cm s$^{-1}$, all while alternating DI water and 0.6 M NaCl solution segments every 20 sec. FIG. 9E depicts current density for Fe:FeOx and Al:AlOx nanolayers as a function of the natural logarithm of the salt concentration difference in solutions of alternating salinity recorded using 30 μL drops at a drop rate of 2 mL min$^{-1}$ (flow velocity=0.3 cm s$^{-1}$, assuming a 0.1 cm$^2$ contact area of the rolling drop). Error bars on point estimates shown are for 1 standard deviation (σ) from n=O (100) replicate measurements. FIG. 9F depicts the natural logarithm of the current density (in A cm$^{-2}$) as a function of change in Gouy-Chapman surface potential (σ=0.007 C m$^{-2}$) resulting from changing the ionic strength when altering the salt concentration.

FIG. 14A depicts atom probe tomography reconstruction of the heterostructured Fe:FeOx nanolayer (center). Iron oxide and iron metal shown separately on top and bottom, respectively. FIG. 14B depicts an all-atom representation of the heterostructured nanolayer, including the metal conductor (gray) and a nonpolarizable oxide overlayer and with columnar subsurface heterostructure (darker outlined circles); a single probe Na+ cation is shown at a distance of 1.6 angstroms from the nanolayer. FIG. 14C depicts induced charge distribution, Q (x), by the Na$^+$ cation at four different lateral positions relative to the position of the nonpolarizable heterostructure. FIG. 14D depicts ion-nanolayer Coulomb interaction as a function of lateral ion position, for various widths, d, of the nonpolarizable heterostructure; $\Delta E^{coul}$ is the difference in the ion-nanolayer Coulomb interaction for the nanolayer systems with and without the subsurface heterostructure. FIG. 14E depicts a molecular dynamics (MD) simulation snapshot for alternating regions of ionized (0.43 M NaCl) water/DI water in contact with the nanolayer with columnar heterostructure (d=1.3 nm). The nanolayer is shown as in FIG. 14B, but with the instantaneous charge polarization of metal conductor atoms also indicated (range=[−0.005 e (black), +0.005 e (dark grey)]). Vertical dotted lines indicate semipermeable boundaries for the ions to preserve the salinity boundaries. FIG. 14F shows, for the simulation cell shown in FIG. 14E, the time-averaged induced charge distribution, Q (x), as well as the 0.5-ns block averages of the same quantity. FIG. 14G shows a comparison of the time-averaged induced charge distribution for the system with and without nonpolarizable heterostructure.

FIGS. 15A-15D depict, for various positions (FIG. 15A—0 nm; FIG. 15B—0.5 nm; FIG. 15C—1 nm; and FIG. 15D—1.5 nm) of a single monocation, the distribution of induced charge in the metallic portion of the nanolayer, Q(x,z), integrated over the y-coordinate of the simulation cell. Nonpolarizable oxide atoms are indicated with darker, solid grey shading. The position of the monocation is indicated with the black circle, illustrating various displacements with respect to the position of the subsurface heterostructure.

FIGS. 21A and 21B. Current (FIG. 21A) and voltage (FIG. 21B) obtained when moving a beaker of a 0.6 molar salt (NaCl) solution up and down over a stationary vertical metal nanolayer of amphoteric nickel oxide/nickel bilayer on glass, resulting in the regular, repeated wetting and dewetting of the metal oxide surface, repeated multiple times.

DETAILED DESCRIPTION

Figure 1B:
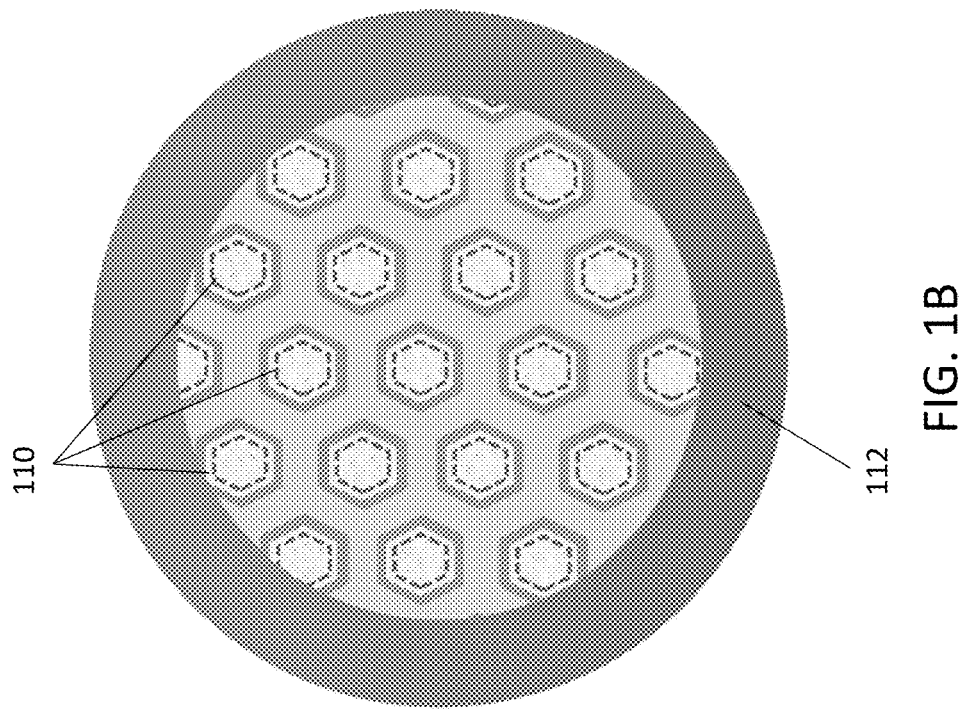
FIGS. 1A-1B.

Energy harvesting devices and methods for converting the mechanical energy of a flowing ionic solution, such as rainwater or seawater, into electric energy are provided. Also provided are flow sensors and methods for using the flow sensors to monitor the flow of an ionic solution, as well as frictionless pumps and methods for using the pumps to move an ionic solution across a surface.

One embodiment of an energy harvesting device (FIG. 1A) includes an electric current generating device that includes a metal substrate composed of at least one metal layer 102 and an amphoteric metal oxide film 104 disposed over a surface of the metal layer. The metal layer, which may be disposed on a support 100, acts as an electrical conductor and, in some embodiments, has a thickness that is no more than an order of magnitude greater than the length of the mean free path of an electron in the metal of the metal layer. The energy harvesting device further includes an electronic device 106 that is powered by the electric current generating device or an energy storage device that is charged by the electric current generating device. Electronic device 106 can be any electrical component that consumes electrical power, such as a light, a computer, or an appliance. In contrast an energy storage device is one that stores electrical power, such as a battery or a capacitor.

Although the inventors do not intend to be bound to any particular theory of the invention, the operation of the device can be considered as follows. When an ionic solution (that is—a solution that contains ions) passes over the amphoteric metal oxide film, an interface is formed between the ionic solution and the amphoteric metal oxide. This interface is characterized by a distribution of anions, cations, and water molecules within electrical double and diffuse layers, which are collectively referred to as the EDL, and the protonation state of the surface hydroxyl groups terminating the oxide. If the amphoteric oxide film is thin enough, the electrostatic potential can reach through the film and polarize the underlying metal. As a result, it is possible to generate an electric current in the conductor beneath the metal oxide overlayer by moving an electrical double layer across it, particularly if the space available for charge mobility in the metal layer is horizontally confined and comparable to the electron mean free path in the conductor. The directional electron flow can be confined by limiting the thickness of the metal layer to the nanoscale using, for example, a dendritic amphoteric metal oxide or other overlayer of lesser electrical conductivity than the conductor on one side of the conductor (for example, the top side), and an insulating support on the opposing side (for example, the bottom side). The directional electron flow can also be confined by limiting the thickness of the metal layer to the nanoscale by using a dendritic amphoteric metal oxide or other overlayer of lesser conductivity on both sides (top and bottom) of the conducting metal layer.

The metal layer can be formed on the support in a single step using a physical or chemical vapor deposition process, such as electron-beam physical vapor deposition (PVD). Electron-beam PVD methods for making high purity metal layers, including iron layers, are described in U.S. Pat. No. 9,738,966. An amphoteric oxide overlayer can form spontaneously on the surface of the metal layer in an oxygen-containing environment, such as ambient air. The metal layer should be grown to a thickness that is comparable to the mean free path of the electrons in the metal from which it is made; this imparts hardness to the layer and facilitates charge motion parallel to the metal layer/metal oxide film interface, as opposed to away from (i.e., perpendicular to) said interface. The metal can be of very high purity so that the growth of the oxide overlayer self-terminates before it reaches a thickness of more than several nm. For example, the metal oxide layer may grow to a thickness in the range from 0.5 to 10 nm. High purity metal layers and self-terminating oxidation result in metal layers and films that are stable and resistant to corrosion and delamination over long periods. The thickness of the metal oxide film can be controlled based on the metal used in the metal layer, the thickness of the underlying metal layer, and the purity of the metal. By way of illustration, the metal layer will typically have a thickness of no greater than, or on the order of, 500 nm and the metal oxide overlayer (also referred to as the metal oxide film) will typically have a thickness of no greater than, or on the order of, 10 nm. This includes embodiments in which the metal layer has a thickness of no greater than 100 nm and further includes embodiments in which the metal layer has a thickness of no greater than 50 nm, and the metal oxide overlayer has a thickness of no greater than 8 nm. By way of illustration, in some embodiments, the metal layer has a thickness in the range from 8 nm to 100 nm, and the metal oxide film has a thickness in the range from about 2 nm to 7 nm.

In some embodiments, the device includes a multilayered film that includes multiple (i.e., two or more) metal layers with the same composition or with different compositions in a stacked configuration. Optionally, each of the metal layers can be oxidized prior to the deposition of the next metal layer to provide a stack of alternating metal layers and metal oxide films. In embodiments where the metal layers in the stack have different compositions, the metal layers and their corresponding metal oxide films can comprise metal alloys or mixtures of different metal elements formed by the co-deposition of the metals. One embodiment of a device that includes a multilayered film. By way of illustration, the metal layers can include an iron layer, followed by a chrominum layer, followed by an aluminum layer or the metal layers can include a first iron layer 102, followed by a second iron layer 122, wherein each metal layer has a corresponding metal oxide overlayer, 104, 144.

In some embodiments of the devices, the metal layer is a high purity, zero-valent iron layer. However, other metals that form thin, self-passivating amphoteric oxides can also be used, wherein an amphoteric oxide is an oxide that can act both as an acid and as a base according to Brönsted-Lowry Theory. These metals include, but are not limited to, aluminum, zinc, copper, tin, chromium, nickel, and vanadium. The amphoterism of the oxide overlayer can be used to determine the sign and magnitude of the charge and potential distributions within an EDL under conditions of varying aqueous pH and ionic strengths. Specifically, the point of zero charge (PZC) of the oxide overlayer may be above or below the pH of the ionic solution, determining whether the surface charge density is positive or negative, respectively. The further away from the PZC the pH is, the larger the magnitude of the oxide overlayer surface charge density. Likewise, for a given oxide overlayer surface charge density, the ionic strength in the ionic solution above the oxide overlayer determines the magnitude of the electrostatic potential emanating from it.

The use of high purity zero-valent iron nanofilms may be advantageous because large area films can be formed using PVD techniques using relatively inexpensive and commercially available standard purity starting materials, as demonstrated in Example 1. In addition, the optical properties of the amphoteric iron oxide overlayers also enable the generation of charge carriers via exposure to visible light. The use of metals having biocidic properties, such as aluminum, zinc, and silver, can be beneficial for protecting against biofilm formation for applications where such formation is undesirable.

In some embodiments of the devices, the metal of the metal layer forms dendrites, which are finger-like structures. These dendrites can be used to facilitate the directional flow of electrons in the layer. Dendrites can be formed when the metal oxidizes in air once vapor deposition is complete. By controlling the oxygen partial pressure, relative humidity, and temperature, the structure, number density, width and depth of the metal oxide dendrites can be adjusted to optimize charge mobility along the potential hotspots on the dendrites and minimize possible leakage due to tunneling.

Metals that form redox-active oxides, that is—oxides that contain the metal in more than one oxidation state, generally produce higher currents. Therefore, embedding metal atoms having multiple charge states, such as chromium and/or iron, in the metal layer can increase the current produced by the devices described herein. In addition, current generation can be increased by increasing the carrier density in the metal oxide overlayer. Therefore, the metal oxide overlayer can be chemically doped with either n-type or p-type extrinsic dopants in order to increase current generation. Such dopants include those commonly employed in semiconductor doping. Embedded atoms and dopants can be introduced into the metals and metal oxides using, for example, chemical vapor deposition. By way of illustration, suitable dopant concentrations include those in the range from $10^{13}$ cm$^{-3}$ to $10^{13}$ cm$^{-3}$. However, concentrations outside of this range can be employed.

In some examples of the devices described herein, the support upon which the metal film is formed is electrically insulating. Examples of materials from which an electrically insulating support can be made include glass, marble, and organic polymers, such as polypropylene or polyethylene. In other embodiments of the devices, the support comprises a layer of magnetic material. In these embodiments, the support may itself be composed of a magnetic material (e.g., the support can be a permanent magnet), or a layer of magnetic material may be disposed on a surface of an electrically insulating support layer, opposite the metal film. The use of magnetic supports is advantageous because, when coupled with a metal layer having magnetic susceptibility (i.e., a material that becomes magnetized in an applied magnetic field), such as nickel, iron, vanadium, chromium, or aluminum, an enhanced current density output can be achieved, as illustrated in Example 7. The metal having magnetic susceptibility also desirably forms a metal oxide having magnetic susceptibility. Generally, a magnetic layer having a higher flux density gradient steepness and a higher surface flux density will provide a greater enhancement in the current density output. A neodymium magnet is an example of a magnetic layer that can used as the support, or as one layer of a support. The supports may be rigid or mechanically flexible.

The electric current generating devices operate by exposing a surface of the amphoteric metal oxide film facing opposite the metal layer/metal oxide film interface to a flow of ionic solution that imparts a varying surface potential on the metal oxide film. The flow rate can vary over a broad range. For example, in some embodiments of the methods for harvesting energy, ionic solution flow rates of at least 0.5 mL/min, at least 10 mL/min, and at least 20 mL/min were used. However, lower flow rates can also be used. The concentration of ions in the ionic solution can be, but need not be, quite low. By way of illustration, the ion concentration level of the flowing liquids used to operate the devices described herein may be in the range from about 0.1 mM to 2 M, including in the range from 0.1 M to 1 M. The flow of ionic solution can be generated by natural phenomena or by non-naturally occurring mechanical means, such as by pumps, including those used for urban discharge management or desalination.

The movement of an EDL across the surface of the metal oxide film can be achieved in several ways. First, intermittent flow of the ionic solution can be passed over the surface. A flow of discrete, separated droplets is an example of an intermittent flow stream. Waves periodically flowing over the device surface are another example of an intermittent flow stream.

However, the ionic solution need not be intermittent. For example, the device can be operated using a flow of ionic solution having a temporal variation in ionic conductivity. A temporal variance in the ionic conductivity can be achieved by using a continuous flow of a liquid stream having a substantially constant flow rate and direction, but a non-uniform ion concentration within the stream along the direction of the flow. An intermittent flow may be a flow of water having a given salinity alternating with air or similarly sparingly miscible matter to sharpen the screening potential gradient along the metal oxide overlayer. This can be achieved by a liquid stream having alternating sections (e.g., plugs) of a first ionic solution having a first ionic conductivity and second sections (e.g., plugs) of a second liquid, which may also be an ionic solution, having a lower conductivity than the first ionic solution. The sections of the second liquid in a continuous liquid stream can be formed from a liquid that is immiscible with the first ionic solution. By way of illustration, a liquid stream comprising aqueous sections interspersed with oil sections in a tube, such as a capillary tube, could be used. Natural bodies of water can also create a liquid flow with a temporally varying ionic conductivity (e.g., temporally varying salinity) to move a screening potential along the metal oxide overlayer to generate a current in the underlying metal layer. For example, the salinity levels in some natural bodies of water, such as some marine environments, estuaries, and fjords, vary with the tidal cycle. Therefore, a water flow generated by the tidal cycle of such bodies of water could be used to provide a liquid flow with a temporally alternating salinity.

The movement of an EDL across the surface of the metal oxide film can also be achieved by using a flowing ionic solution that has a temporally varying flow rate and/or a temporally varying flow direction. A temporally varying flow rate can be achieved by modulating the velocity of an ionic solution stream as it flows over the surface of the device. For example, the flow rate of the ionic solution can be modulated from a first (higher) flow rate to a second (lower) flow rate and then to higher flow rate again in repeated cycles; that is—the ionic solution can undergo cyclic fast-slow flow. Instead of, or in addition to, the flow rate, the direction of flow can also be modulated to create a flow with an oscillating direction over the device surface. For example, the direction of the ionic solution flow can be changed from a first direction (e.g., forward flow) to a second direction (e.g., backward flow) in repeated cycles to induce a varying potential in the metal layer of the device. For embodiments of the methods that rely on a varying flow rate and/or a varying flow direction, the ionic concentration of the flowing solution can remain constant throughout the flow process.

One application for devices that use ionic solutions with temporally varying flow rates is as blood flow sensors or as blood flood energy harvesting devices, since blood is an ionic solution that is naturally pumped with a temporally varying flow rate. Thus, the devices described herein can be used in vitro or implanted in vivo in a vein or artery such that blood flowing over the amphoteric metal oxide film generates a current in the metal substrate. The resulting current can be used as the basis for a blood flow rate sensor or as the basis for an energy harvesting device.

It should be noted that the use of varying flow rates, varying flow directions, and varying ion concentrations are not mutually exclusive. In some embodiments of the devices, one or more of the flow rate, the flow direction, and the ion concentration of the ionic solution flow may change as the flow passes over the amphoteric metal oxide of the devices.

The ionic solution can be a solution containing solvated ions and having a sufficiently high ion concentration to generate an electric current. For example, an aqueous salt solution, including rainwater or salinized water or brine from a natural body of water, such as a sea or a river, with an ionic strength as low as 0.1 mM, can be utilized. Other sources for an ionic solution include waste brine from a water desalination facility, wastewater from a wastewater treatment plant, urban water discharge, ground water, and glacier water. However, other ionic solutions, including liquid containing salts other than sodium chloride can be used. For example, other ionic salts, including other halide salts can be used. Such salts include both monovalent salts and multivalent salts, such as $YCl_3$, as illustrated in Example 2 and Example 3.

As discussed above, some embodiments of the devices utilize a flow of droplets, including, for example, raindrops, for flow induced power generation. In embodiments of these devices, a flow of the liquid droplets falls onto the surface of the amphoteric metal oxide film and slides down the surface under the force of gravity. As the droplets pass over the surface, they generate a unidirectional electron current in the metal layer by moving a screening potential along the metal oxide film. Raindrop-induced power generation can be implemented by using a window for a building as the support for fabricating the current generating device. Because the metal layers and their metal oxide films can be made optically transparent to visible and solar radiation, they can be formed using a window for a building as a support. Since the ionic strength of rainwater (~0.2 mM) is sufficiently high to polarize the interface, the resulting window could be used to harvest power from the raindrops and/or act as a rain sensor. Other ionic solution sources that could be used to provide a discontinuous flow of an ionic solution include waves and tides.

As illustrated in FIG. 1B, stacks or rows of the current generating devices 110 can be built into a pipe 112 or channels, and wave action, propulsion, ocean currents, or tidal movements due to gravitational forces from outside the earth can be used to generate a flow of salt-containing water through or over the electric current generating devices. This approach can satisfy an operational requirement of having to move a dynamically changing electrical double layer structure across the metal oxide film, and do so over long distances. By coupling (e.g., connecting in parallel or series) a plurality of the current generating devices, substantial power generation can be achieved.

Figure 1A:
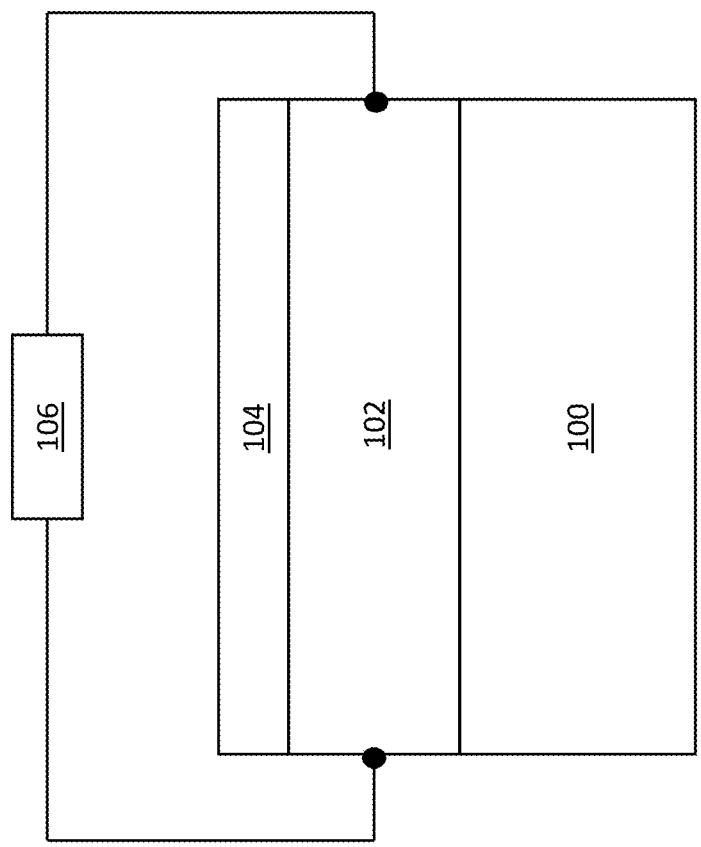

The current generated in the metal layers of the current generating devices can be harnessed by connecting an electrical device, such as a household appliance, or an electrical energy storage device, such as a capacitor or battery, laterally across the metal layer. For the purposes of this disclosure, an electrical device or a storage device can be considered connected "laterally" across the metal layer as long as it is connected in such a configuration that the directional current generated in the metal layer and moving parallel to (as opposed to perpendicular to) the metal/metal oxide interface provides power for the electronic device or charges the storage device. The connection may include additional active or passive electronic components, and the electrical device or the storage device can be connected across more than one current generating device. As shown in FIG. 1A, a lateral connection across the metal layer can be a connection from one edge of the metal layer to the opposing edge.

The current generating devices can also be used as flow sensors. One basic embodiment of a flow sensor includes a current generating device, as described herein, and a voltage measuring device, such as an oscilloscope, or a current measuring device connected laterally across the metal layer of the current generating device in a configuration whereby the voltage or current measuring device measures the voltage across, or current through, the device as a flow of an ionic solution passes over the surface of the amphoteric metal oxide film. The general structure of a flow sensor is shown in FIG. 1A, where reference number 106 represents a voltage measuring device or current measuring device, rather than an electronic device. (The relative thicknesses of the layers in FIG. 1A are not to scale.)

The devices also can be run in "reverse", whereby droplets of an ionic solution can be moved across the surface of the amphoteric metal oxide film by, for example, putting in non-Faradaic currents or applying a voltage across an ionic solution disposed on the amphoteric metal oxide. As such, the devices can operate as a silent and frictionless pump without any moving parts to move ionic solutions against the force of gravity, as illustrated in Example 4.

EXAMPLES

Example 1

This example reports kinetic:electrical energy transduction using nanolayers formed in a single step from earth-abundant elements. The method utilizes large-area PVD onto rigid or flexible substrates that can be readily scaled to arbitrarily large areas. In addition to flowing aqueous droplets across the nanolayers, current is shown to be created either with linear flow of salinity gradients or with oscillatory flow of a constant salinity. The operational principle of moving a dynamically changing electrical double layer (a "gate") across the nanostructure identified in prior approaches is confirmed for the new structures and augmented by occurrence of electron transfer within the thermal oxide nano-overlayers terminating the metals. The simplicity of the approach allows for rapid implementation. This example illustrates the formation of single- and dual-element nanolayers from low-cost 99.95% purity iron, 99.98% Ni, 99.7% V, 99.9995% aluminum, and 99.994% chromium sources. XPS reveals a lack of common low-boiling point contaminants like calcium, magnesium, sodium, or zinc in the iron nanolayers and shows the presence of an ~3 nm thin oxidized iron nano-overlayer. Grazing incidence angle X-ray diffraction (XRD) experiments indicate the presence of crystalline $Fe^0$ with low index faces exposed but no crystallinity of the iron oxide overlayer. Control experiments show that this nano-overlayer forms spontaneously when the iron nanolayer is exposed to air and remains stable over prolonged (years) periods of time. Raman and XPS spectroscopy of the iron nanolayers indicate that the oxide nano-overlayer is composed of some Fe (III), $Fe_3O_4$, and other forms of iron oxide. Given the nm-scale spatial variation of the oxide nano-overlayer thickness revealed by the atom probe tomography (APT) experiments, corresponding heterogeneities are expected in the electrostatic potentials—and charge distributions—in the metal below as well.

Fe:FeOx nanolayers having 5, 10, 20, and 50 nm thickness were prepared, which differed in their transparency. 5 and 20 nm thin Al:AlOx and 10 nm Cr:CrOx, V:VOx, and Ni:NiOx nanolayers were also prepared. Nanolayers were deposited onto 3×1 in$^2$ as well as 3×9 inch glass microscope slides. The small slides were placed into a small Teflon cell containing a flow channel (6 mm×7.5 mm×35 mm) Viton-sealed to the metal nanolayers. The large slides were covered with a 1 mm thick silicone sheet into which a 180 mm×15.2 mm wide opening was cut that was then covered by a 1×3×8 in$^3$ Kalrez block containing an in- and outlet fitting (NPT) to connect to a dual pump flow system and waste. After layering a second silicone sheet and a plexiglass cover on top, this large cell was sealed using large-area mechanical clamps.

Aqueous solutions consisted of DI water containing varying amounts of NaCl, equilibrated with ambient air, thus reaching a pH of 5.8. For higher salt concentrations up to 2 M, the pH was adjusted to 8, given the relevance to ocean water and brine. "Instant Ocean" was used as well. Second harmonic generation $\chi^{(3)}$ measurements of the iron nanolayer indicated a negative interfacial charge density of −0.007 (3) C m$^{-2}$ at pH 7, consistent with a considerable number density of deprotonated Fe—OH groups at the oxide/water interface near neutral pH. The change in interfacial electrostatic potential, $\Phi$ (0), or "gate" voltage, estimated from Gouy-Chapman theory, would then be in the −100 mV range when changing the salt concentration from 0.1 mM to 1 M.

Figure 2A:
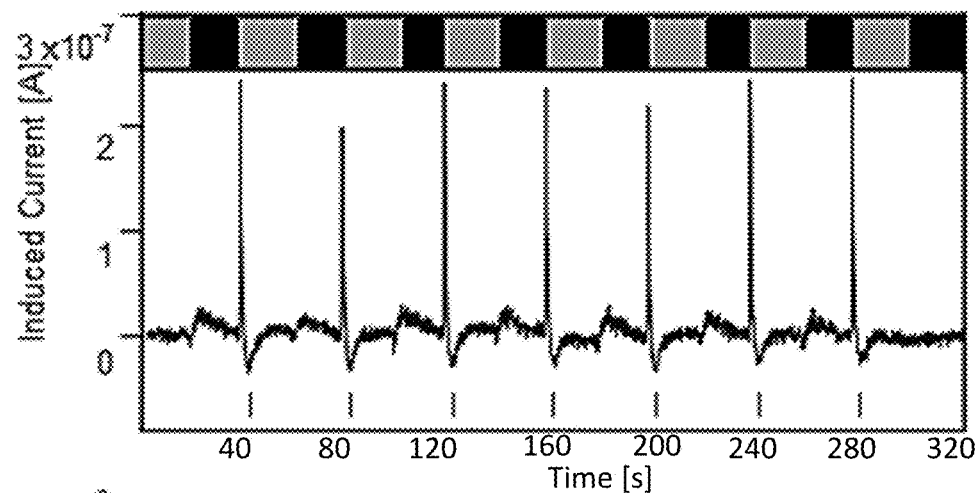
FIGS. 2A-2C: Current and Voltage Measurements.
Figure 2B:
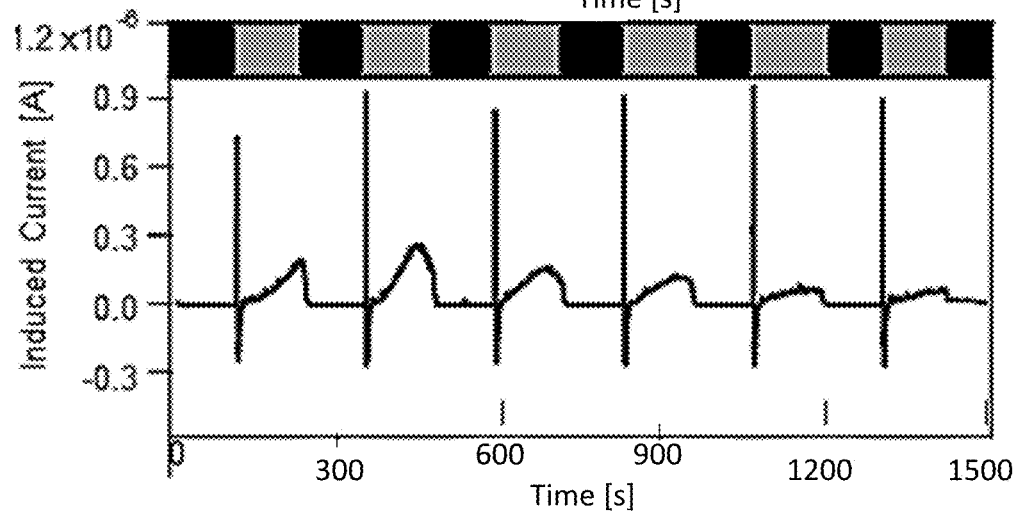
Figure 2C:
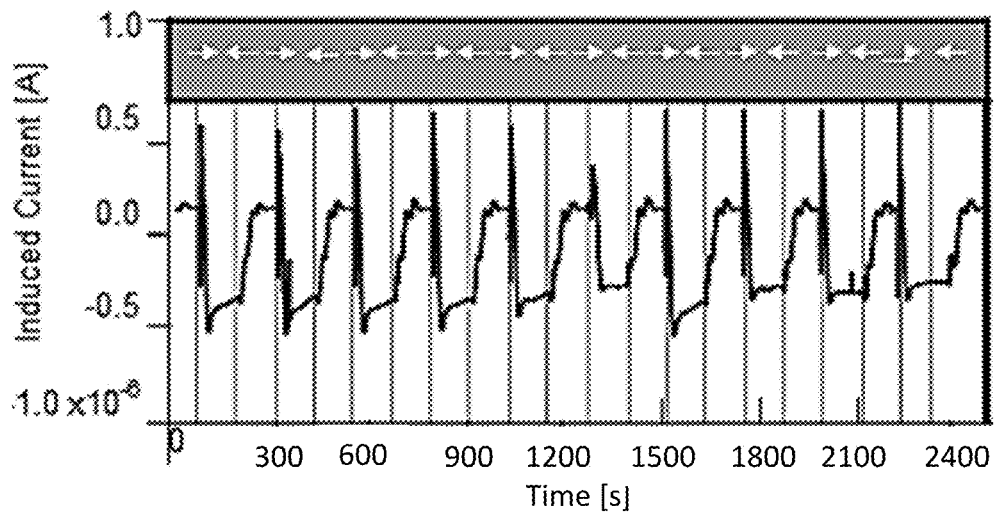
Figure 3:
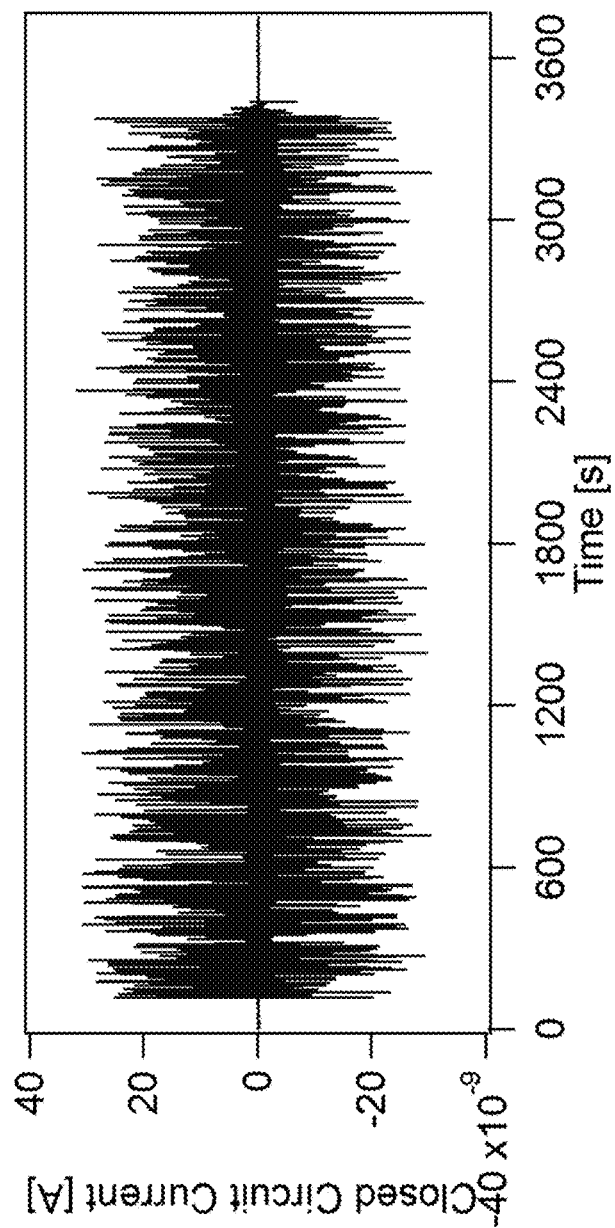
FIG. 3 depicts closed circuit current for a 10 nm thin iron nanolayer under flow of 600 mM NaCl at pH 8.0 lasting 2 seconds alternating with air flow lasting 2 seconds at a flow rate of 28 mL min$^{-1}$.

When flowing water of alternating salinity at 20 mL min$^{-1}$ across a ~10 nm thin Fe:FeOx nanolayer in the small cell, currents of ~0.2 µA (FIG. 2A) and voltages in the mV range were recorded. Currents approaching 1 µA were obtained in the large cell (FIG. 2B, note that the ionic strength gradient in the large cell was about ten times larger than that of the small cell, vide infra). When periodically alternating the direction of aqueous flow at constant ionic strength and constant flow rate in the large cell, current was generated as well (FIG. 2C), albeit in an asymmetric I vs. t pattern attributed to the differences in inlet vs. outlet size in the flow cell used. Current was also generated when alternating aqueous solutions of 600 mM NaCl with air (FIG. 3), albeit at a smaller magnitude compared to continuous aqueous flow.

Figures 4A, 4B:
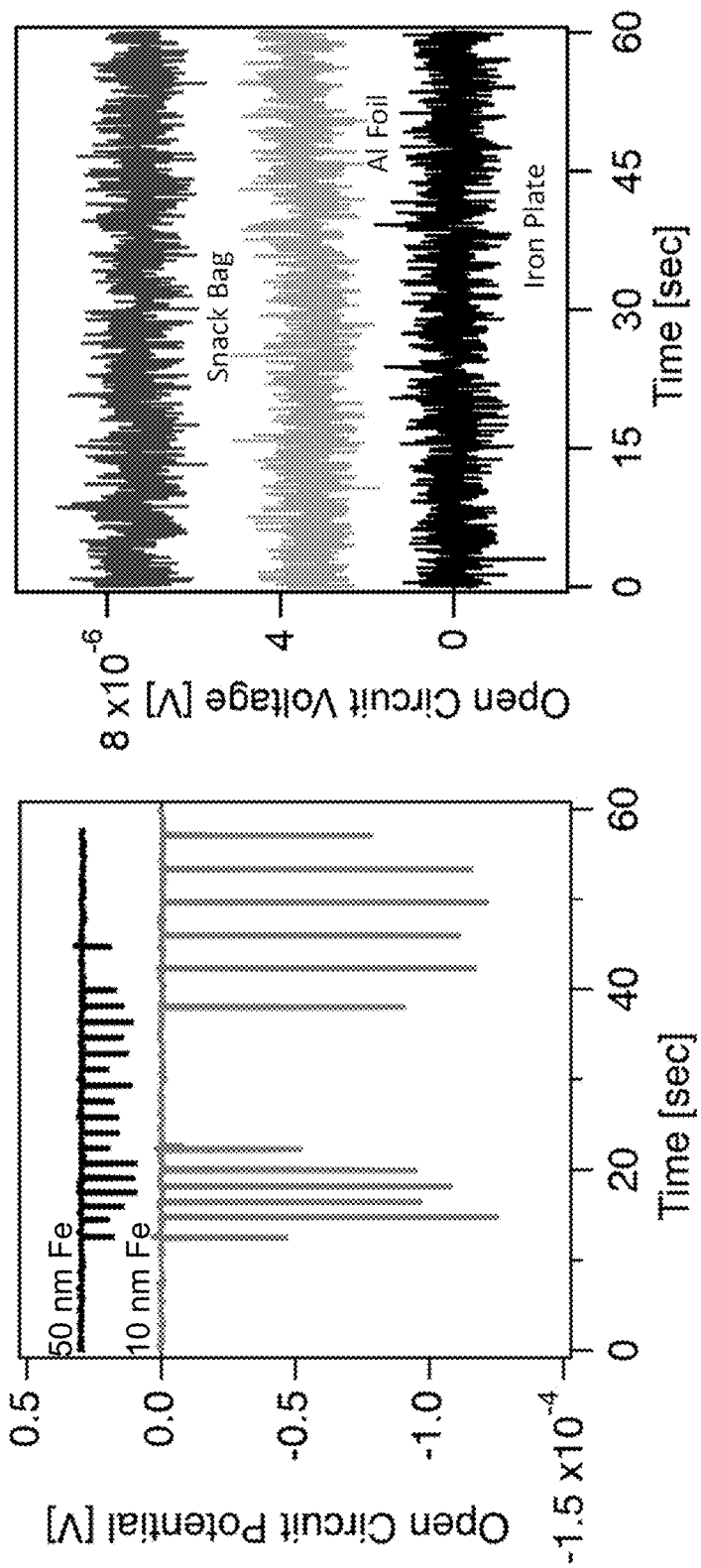
FIGS. 4A-4B.
Figures 5A, 5B:
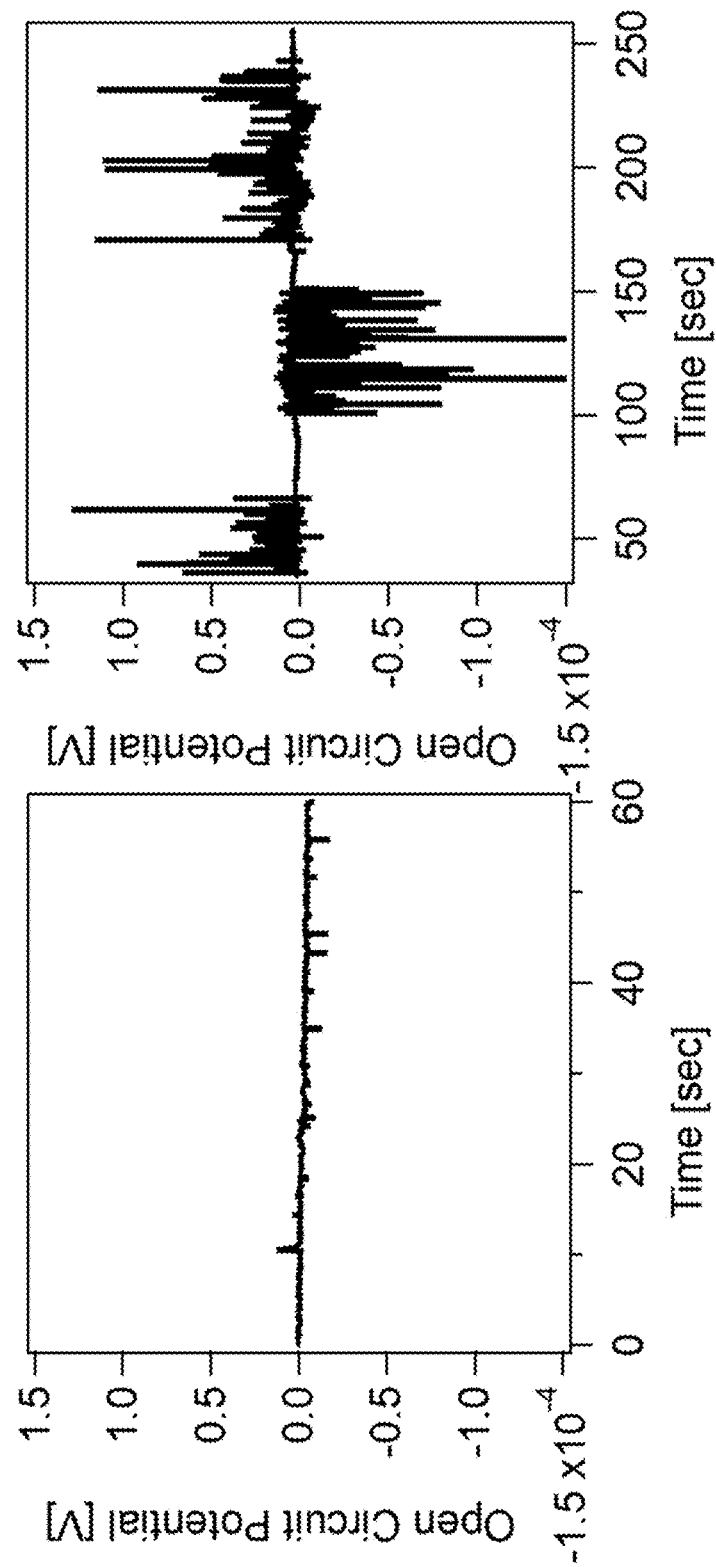
FIGS. 5A-5B.
Figure 6:
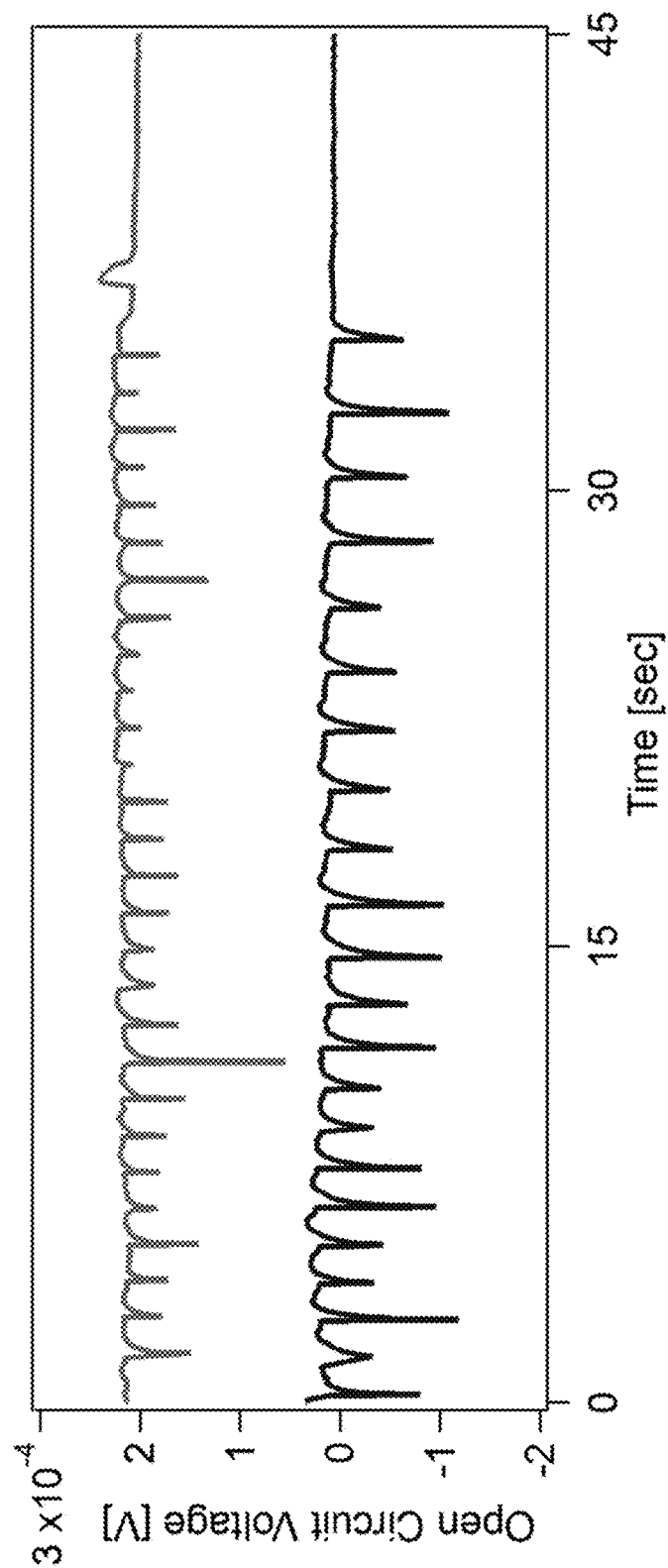
FIG. 6 depicts OCV for a 10 nm thick iron nanofilm using 600 mM salt (top, pH 5.8, offset by 0.2 mV for clarity) and Instant Ocean (bottom, pH 8.3) (drop rate=0.5 mL min$^{-1}$).
Figure 7:
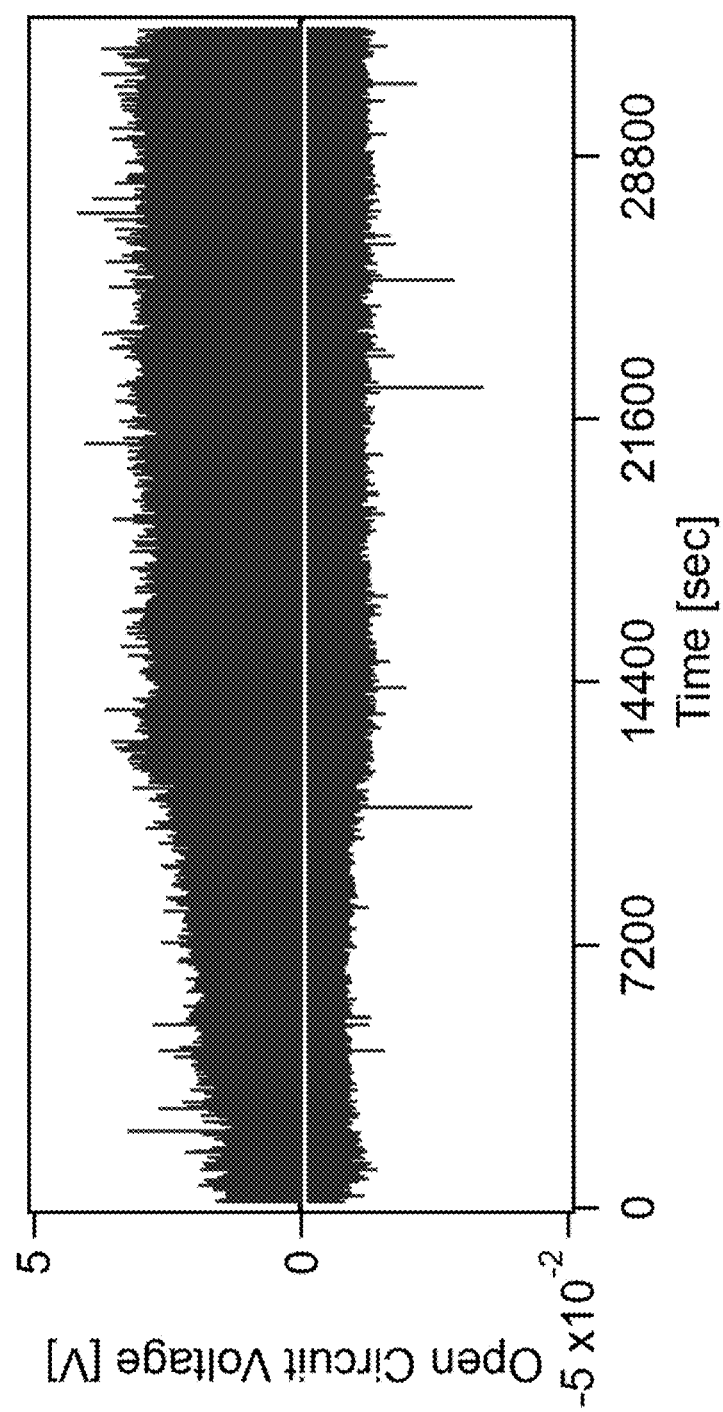
FIG. 7 depicts OCV for a 10 nm thick iron nanofilm using drops alternating between 0.2 mM NaCl at pH 5.8 and 600 mM NaCl at pH 8.0 with a drop rate of 0.5 mL min$^{-1}$.
Figure 8A:
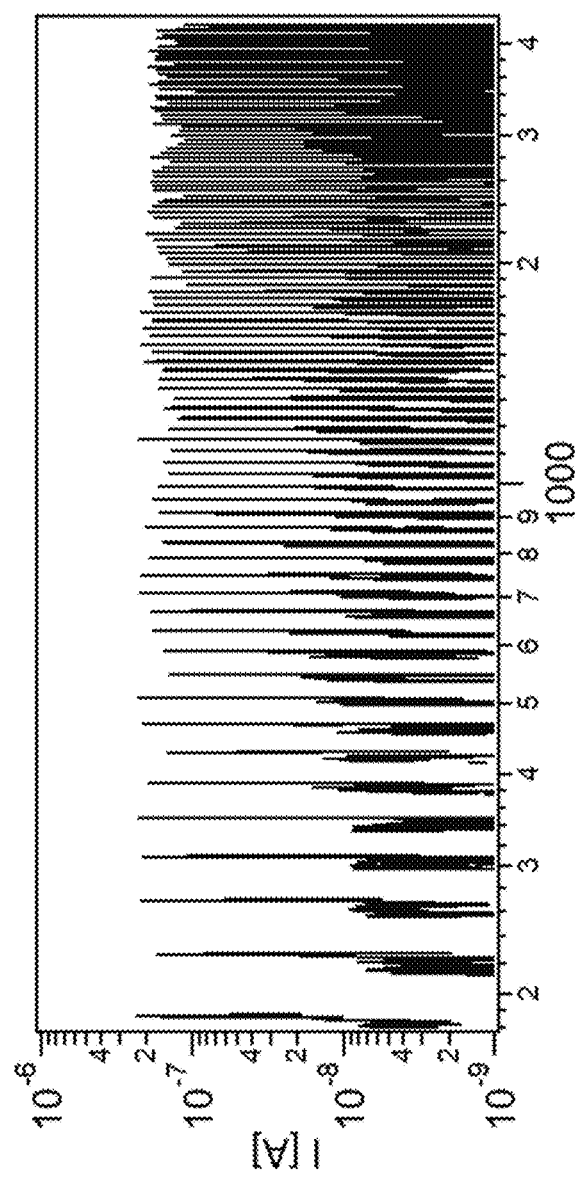
FIGS. 8A-8B.
Figure 8B:
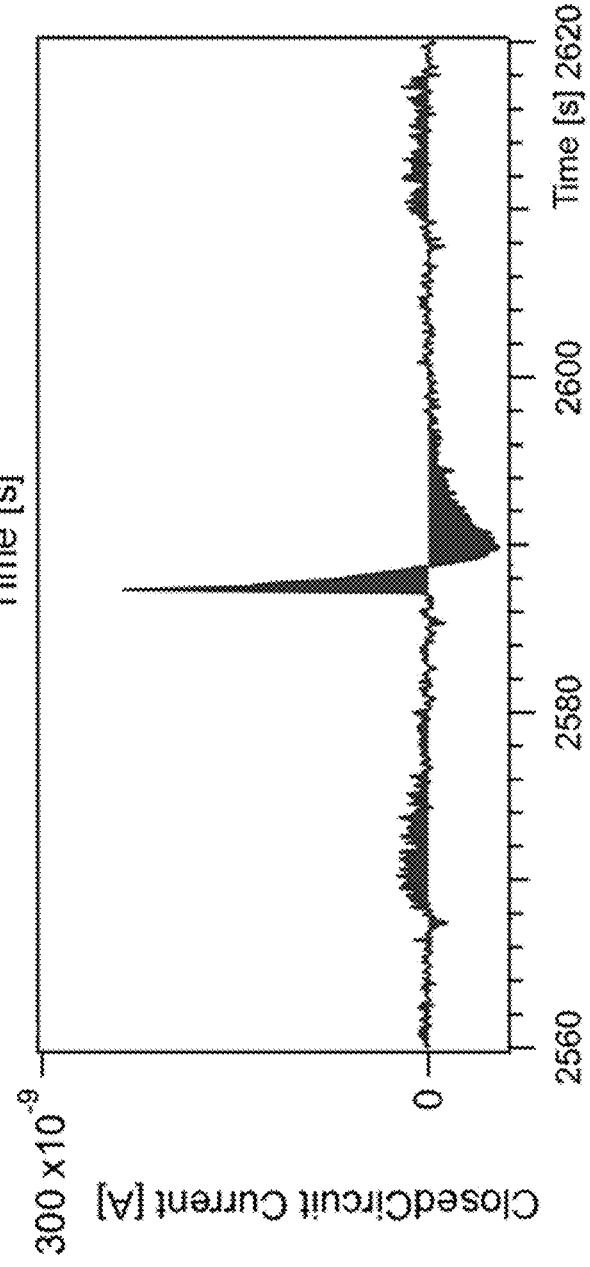

Controls using open circuit voltage measurements show that increasing the iron layer thickness to 50 nm (measured via ellipsometry) leads to considerably smaller open circuit potentials when compared to thinner layers (FIG. 4A), while commercially available aluminum foil, aluminized polypropylene constituting a snack bag wrapping (~100 nm metal layer), a 2 mm thick sheet of iron metal (Alfar Aesar, 99.995%), or aluminum containing its native (thermal) oxide layer show no induced voltage (FIG. 4B). When using drops as opposed to continuous aqueous flow, it was found that measuring the potential across as opposed to along the direction of drop motion shows little voltage during drop motion (FIG. 5A), and that reversing the polarity of the probes reverses the sign of the measured open circuit potential (FIG. 5B). 0.6 M salt solutions representing the salinity of ocean water induce larger voltages than 0.1 M salt solutions that are comparable to those when using "Instant Ocean" (FIG. 6). Alternating the drop salinity between that of the ocean (0.6 M, pH 8) and rainwater (0.2 mM, pH 5.8) induces regular current spikes over >8 hours (FIG. 7). Using the small flow cell, the dynamics of the current flow can be correlated with the flow dynamics inside the flow cell (FIGS. 8A and 8B) for further improvement. Still frames from video recordings using clear and purple-colored water sources reveal a sharp concentration gradient in the flow cell during the time of maximum current generation, from which the "gate" footprint is conservatively estimated to be 7.5 mm channel width×2 mm gradient width for subsequent estimations of current density, j, in the small cell. A similar analysis of the gradient in the big cell shows its footprint is ~2 cm. Alternating the salinity in drop experiments (FIGS. 8A and 8B) produces several tens of mV in open circuit potential that are stable for hours. Additional experiments show induced currents and voltages with an external load resistance of up to 0.5 megaohm placed in series with the nanolayer. Of over 100 metal nanofilms prepared for this Example, each produced comparable current (within a factor of 2) for comparable conditions of nanolayer thickness, flow cell dimensions, flow velocity, aqueous phase composition, and metal type.

Figures 9A, 9B:
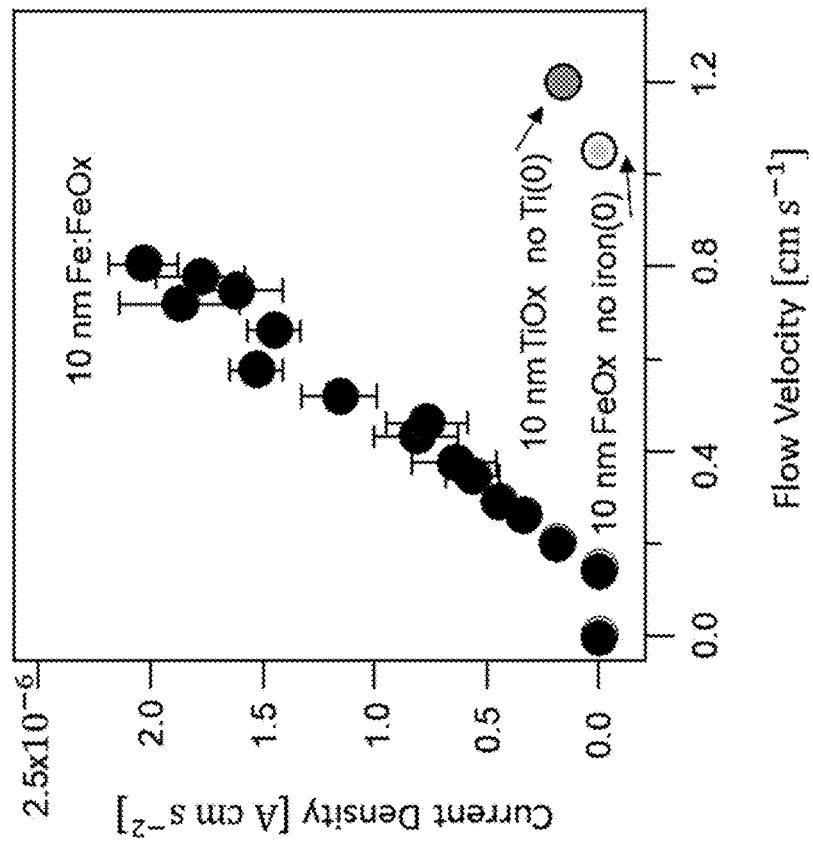
FIGS. 9A-9F: Mechanistic Investigations.
Figure 10:
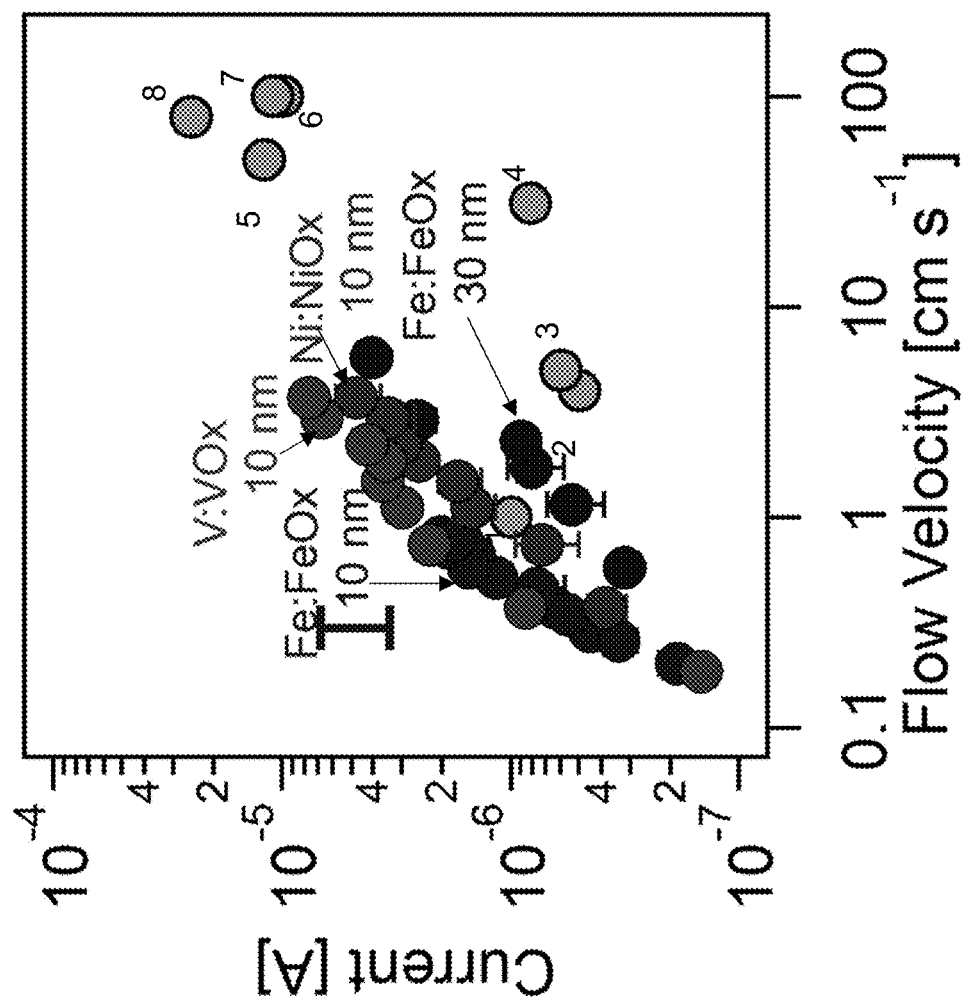
FIG. 10 depicts a plot of FIG. 9B including references provided for the comparison to previously reported results (light grey filled circles).1=A. T. Liu et al., *Advanced Energy Materials* 8, 1 802212 (2018); 2=H. Zhong et al., *Applied Physics Letters* 106, 243903 (2015); 3=J. Park et al., *Journal of the American Chemical Society* 139, 10968-10971 (2017); 4=Q. Tang, X. et al., *Angewandte Chemie International Edition* 55, 5243-5246 (2016); 5=G. Zhu et al., *ACS Nano* 8, 6031-6037 (2014); 6=S. Yang et al., *Journal of the American Chemical Society* 140, 13746-13752 (2018); 7=Yin et al., *Nature Communications* 5, 3582 (2014); 8=W. Huang et al., *Nanoscale* 6, 3921-3924 (2014).
Figure 11:
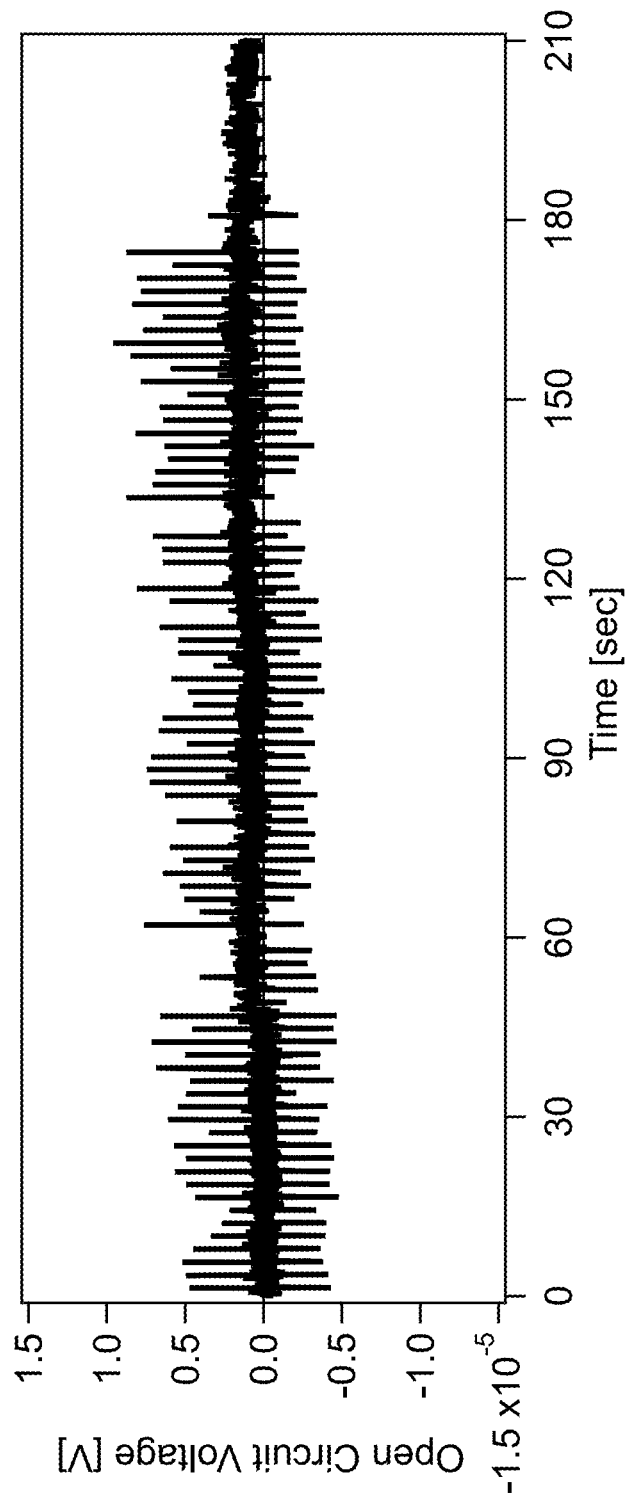
FIG. 11 depicts OCV measured for a 20 nm thin aluminum nanofilm using 600 mM salt (pH 5.8) and a drop rate of 0.5 mL/min.
Figures 12A, 12B:
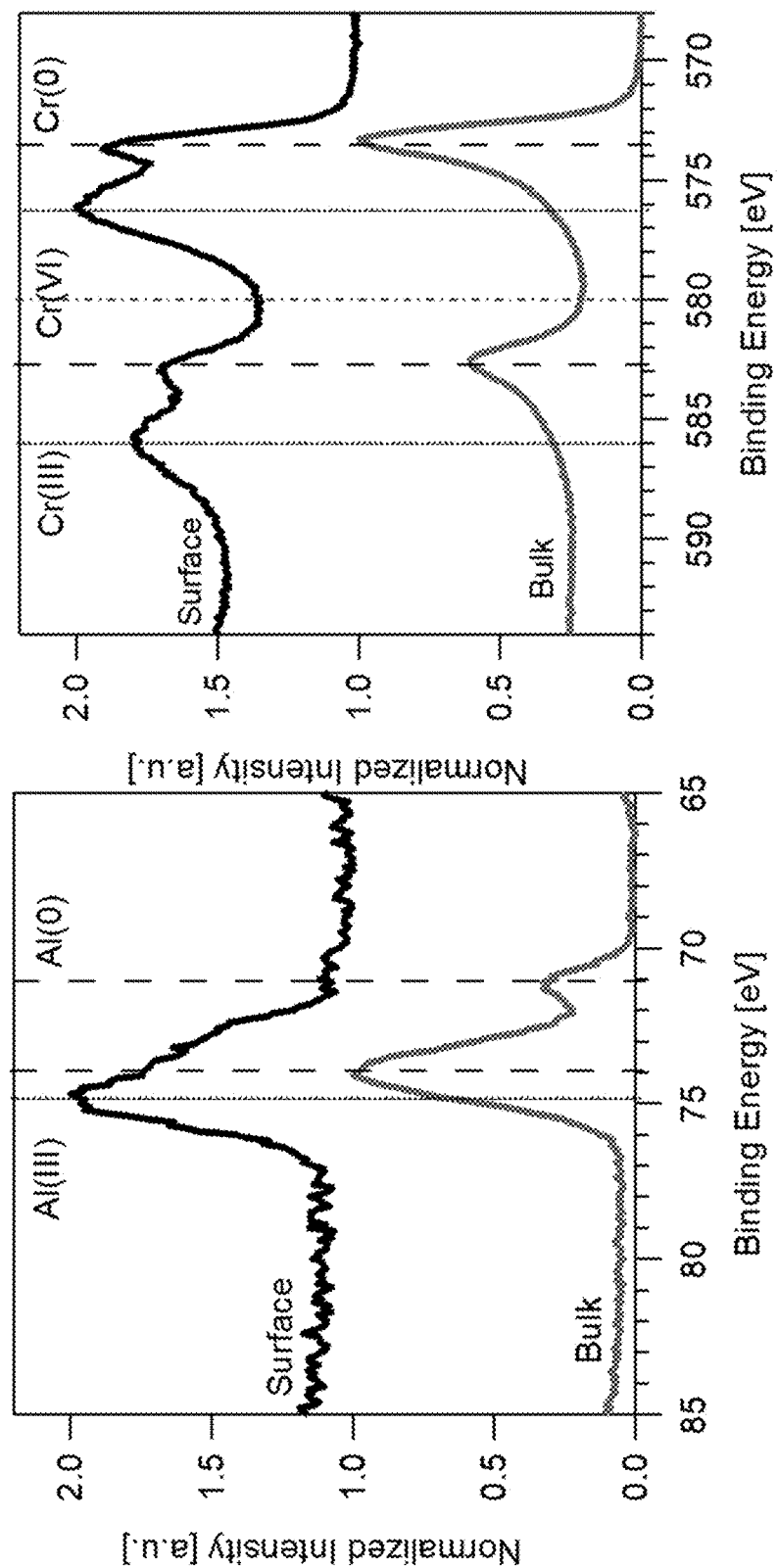
FIGS. 12A-12E depict X-ray photoelectron spectroscopy (XPS) depth profile graphs of ~10 nm (FIG. 12A) Al:AlOx, (FIG. 12B) Cr:CrOx, (FIG. 12C) V:VOx, (FIG. 12D) Fe:FeOx, and (FIG. 12E) Ni:NiOx films deposited on microscope slides. Big and small black dashed lines represent peaks for zero-valent and trivalent/divalent forms of the elements identified, respectively. The dashed vertical line in FIG. 12B shows the absence of hexavalent chromium [Cr (VI)] peaks in the CrOx nano-overlayer. Vertical dotted lines in FIG. 12C show the presence of V(IV) and V(V) in the VOx nano-overlayers, while the dashed lines show V(0). Vertical solid lines in FIG. 12D and FIG. 12E show the presence of M(II) and M(III) in the FeOx and NiOx nano-overlayers.
Figure 12D:
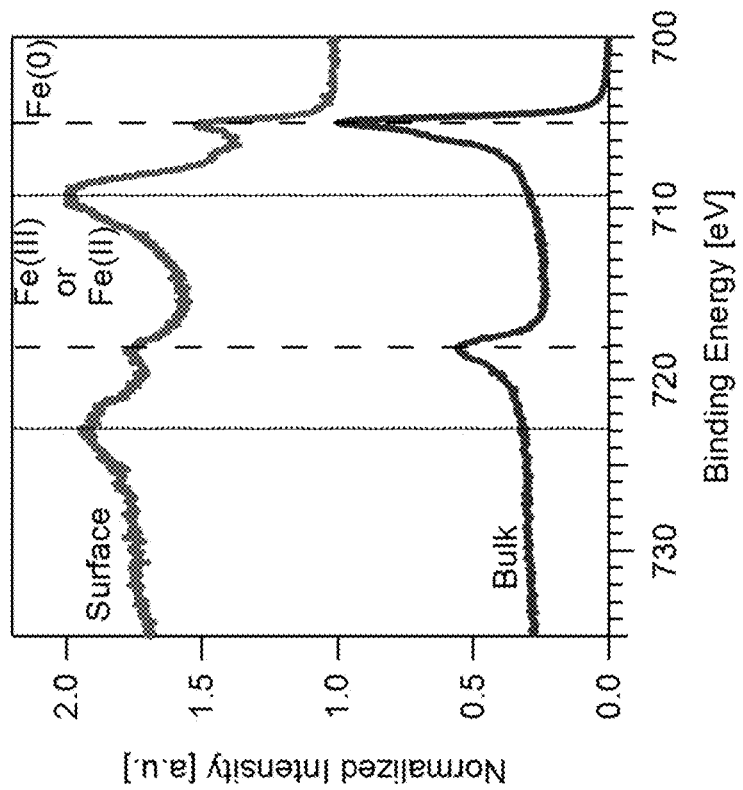
Figure 12C:
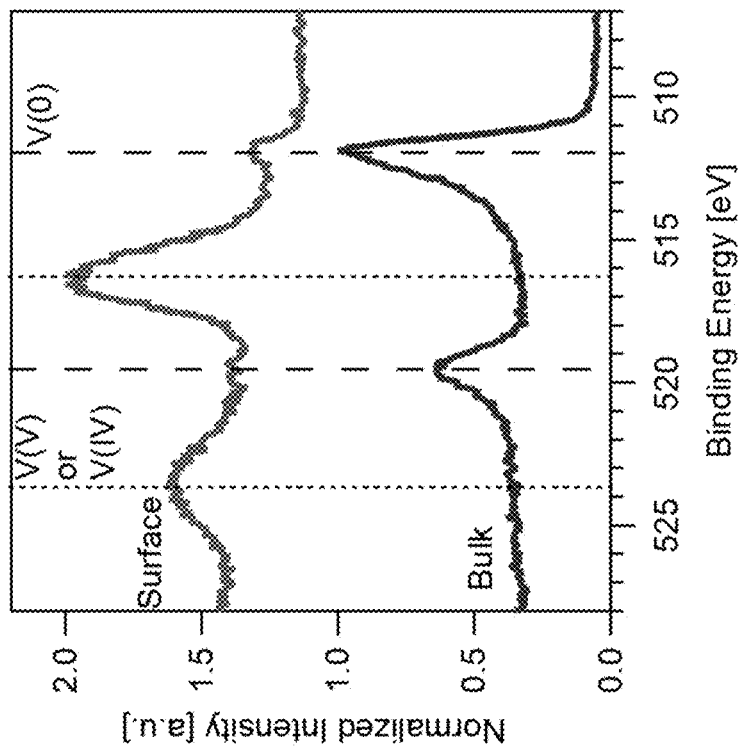
Figure 12E:
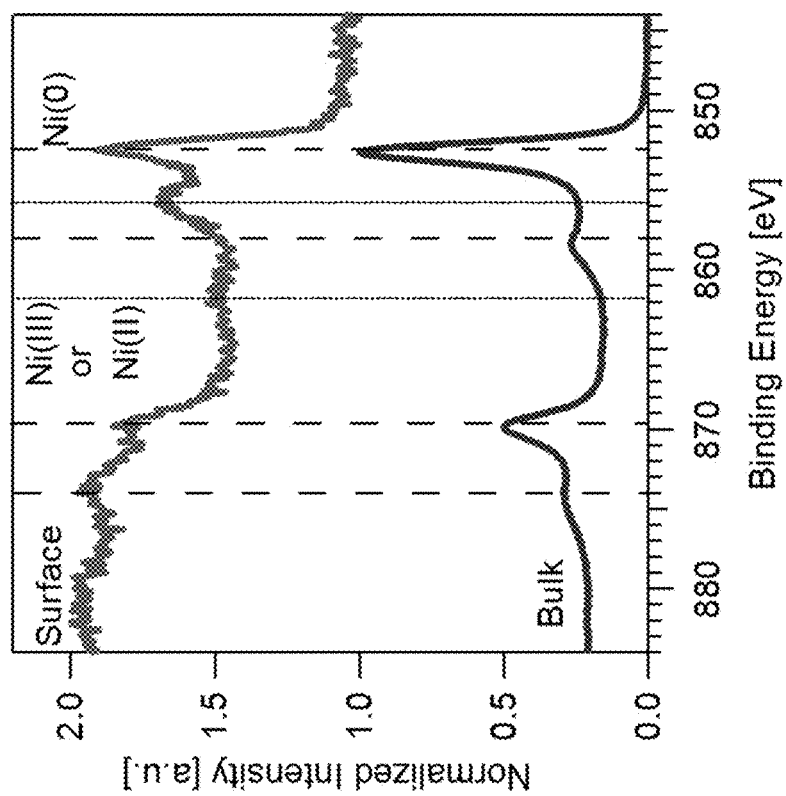

To gain a mechanistic understanding of current generation in the metal nanolayers, a series of experiments were carried out, as described next. FIG. 9A shows that Fe:FeOx, Ni:NiOx, and V:VOx nanolayers of 10 nm thickness produce currents that increase linearly with increasing flow rate at a rate of ~1 to ~3 microA cm' per cm s$^{-1}$ increase in flow rate. The induced current densities are comparable to what can be achieved with falling water drops (vertical line). The produced currents are also comparable to what has been reported previously but obtained with considerably lower flow velocities when using 10 nm or 30 nm thin iron nanolayers or 10 nm thin nickel nanolayers (FIG. 10). (J. Yin et al., Nature Nanotechnology 9, 378-383 (2014); and J. P. G. Tarelho et al., Mat. Today 21 (2018).) Given that the iron oxide nano-overlayers contain iron in multiple oxidation states, it was then investigated whether metal nanolayers terminated with redox-inactive oxides would produce smaller currents. Indeed, FIG. 9A shows that 10 nm thin metal nanolayers prepared from Cr and Al produce considerably less current than 10 nm thin nanolayers prepared from Fe, Ni, or V at comparable flow conditions. FIG. 11 shows a 20 nm Al:AlOx nanolayer also produces considerably less open circuit potential than the Fe:FeOx, Ni:NiOx, or V:VOx layers of comparable thickness. These results are rationalized by the observation that the iron, vanadium, and nickel nanolayers are terminated by thermal oxides that contain Fe(II) and Fe(III), V(IV) and V(V), and Ni(II) and Ni(III), respectively, whereas the aluminum and chromium metal nanolayers are terminated by thermal oxides that only contain metal in the +3 oxidation state (FIGS. 12A-12E).

Figure 9D:
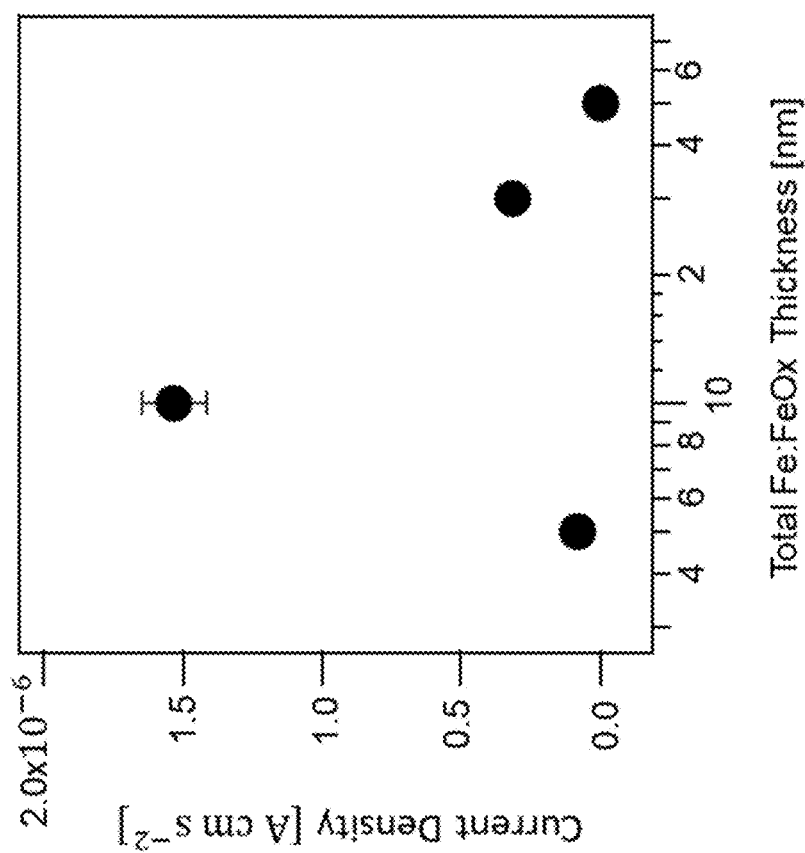
Figure 9C:
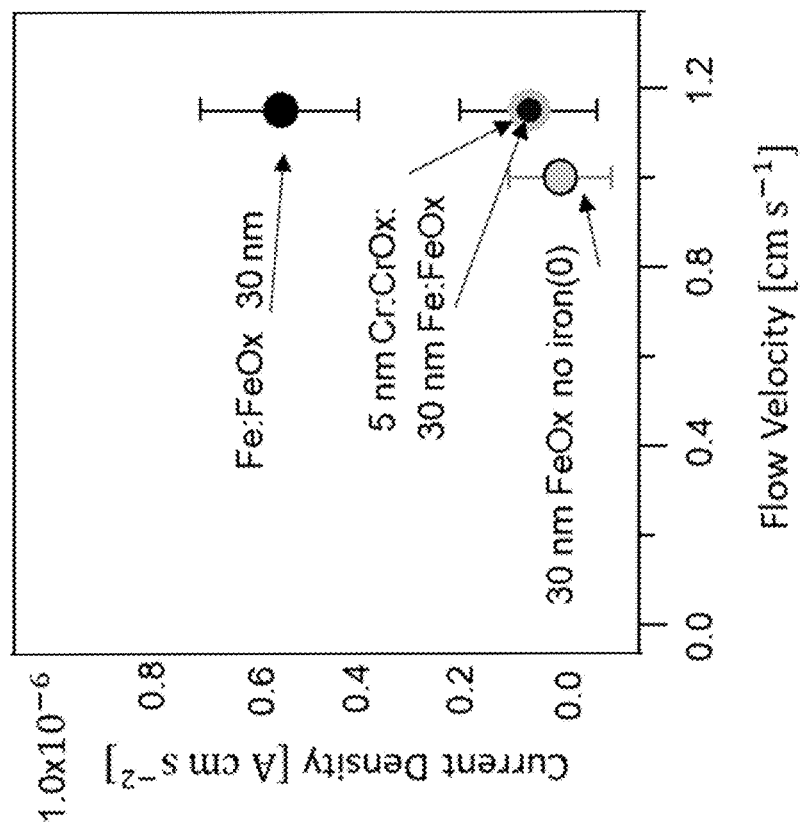
Figure 9F:
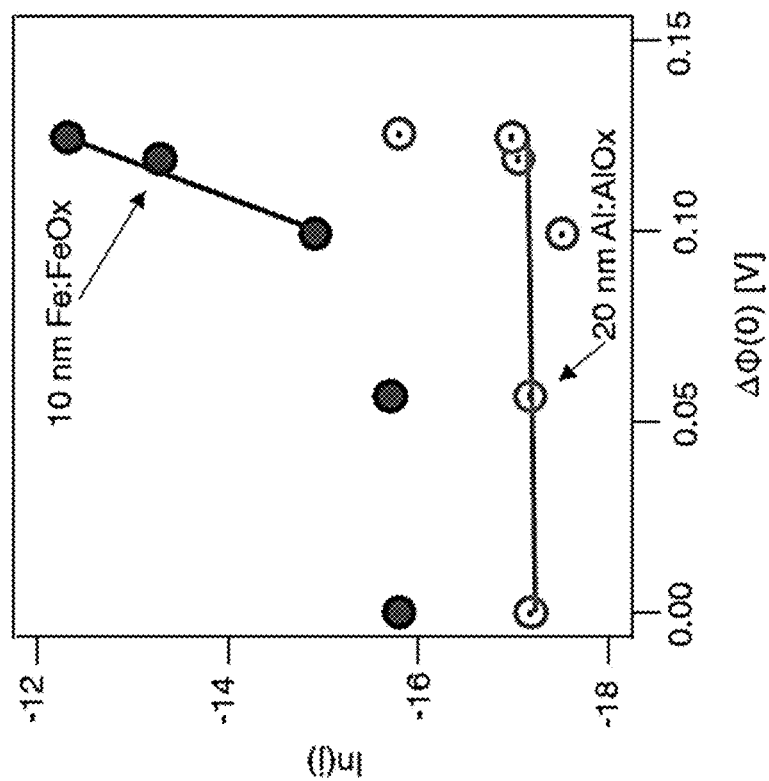
Figure 9E:
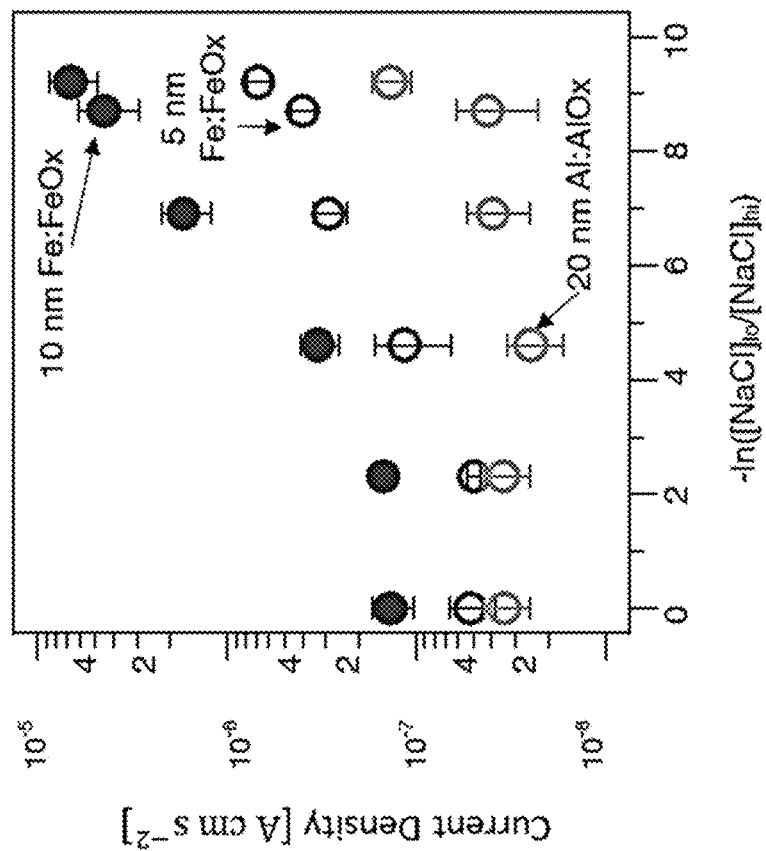

The absence of metal results in negligible current, as shown in FIG. 9B for a 10 nm thin nanolayer of FeOx (no Fe(0) present) prepared by high-temperature quantitative ozone oxidation of a 10 nm thin nanolayer of Fe:FeOx. FIG. 9C shows that a 10 nm thin Fe:FeOx structure produces the highest currents when compared to thinner (5 nm) or thicker (30 nm and 50 nm) layers.

Given the results with the six different systems described in FIGS. 9A-9B, it is expected that covering an active nanolayer (Fe:FeOx or Ni:NiOx) with a less active one (Al:AlOx or Cr:CrOx) should diminish the current density. Indeed, coating a 30 Fe:FeOx nanolayer with 5 nm Cr:CrOx results in considerable current reduction when compared to the neat Fe:FeOx nanolayer (FIG. 9D).

Taken together, the data shown in FIGS. 9A-9D demonstrate that intra-oxide electron transfer between $M^{m+}$ and $M^{n+}$ contributes to the current generation to a larger extent than would be expected from image charge formation alone in metal layers terminated by a redox inactive thermal oxide. Moreover, it is expected that current generation can be further optimized by varying the nature and thickness of the metal and metal oxide layers in mixed metal architectures, alloys, or patterned nanolayers.

The experiments described here additionally support the notion that surface charging of the metal oxide surface is an important part of the current generating mechanism in the metal nanolayers reported here. To explore this hypothesis, the electrical current was recorded as a function of the change in surface potential that occurs when changing the ionic strength from low to high salt concentration. To do so, the current was measured while changing the ionic strength from a given low salt concentration, for example, 0.1 mM, to 1 mM salt for several cycles, and then those measurements were repeated for increasingly higher salt concentrations, each time starting at 0.1 mM (FIG. 9C). The largest currents are induced when the ionic strength difference is largest for each system studied. Experimental surface charge density estimates from second harmonic generation $\chi^{(3)}$ measurements were then used to compute the change in Gouy-Chapman surface potential at the oxide/water interface for each ionic strength difference. FIG. 9D shows that the slopes in these "Tafel" plots are 110 (+/−20) V$^{-1}$ for the Fe:FeOx system. The Al:AlOx system, which is redox inactive under the conditions of these experiments, shows a slope of 7 (+/−2) V$^{-1}$ for all Gouy-Chapman surface potential differences surveyed except the highest, underscoring the large differences between the surface charging of the Al:AlOx and Fe:FeOx nanolayers.

Figure 13:
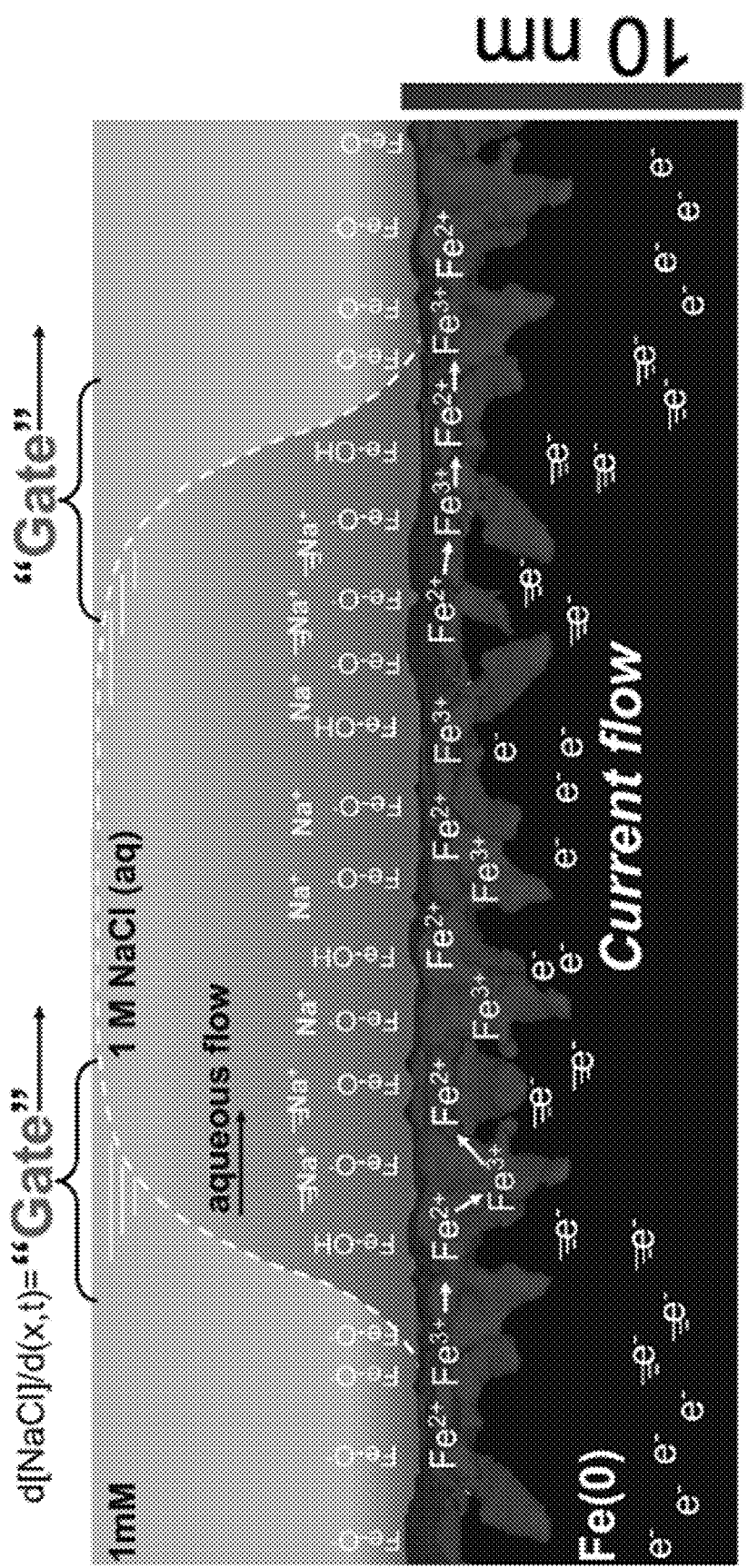
FIG. 13 is a cartoon representation of electrical energy conversion in metal nanolayers terminated by their thermal oxides.
Figure 14A:
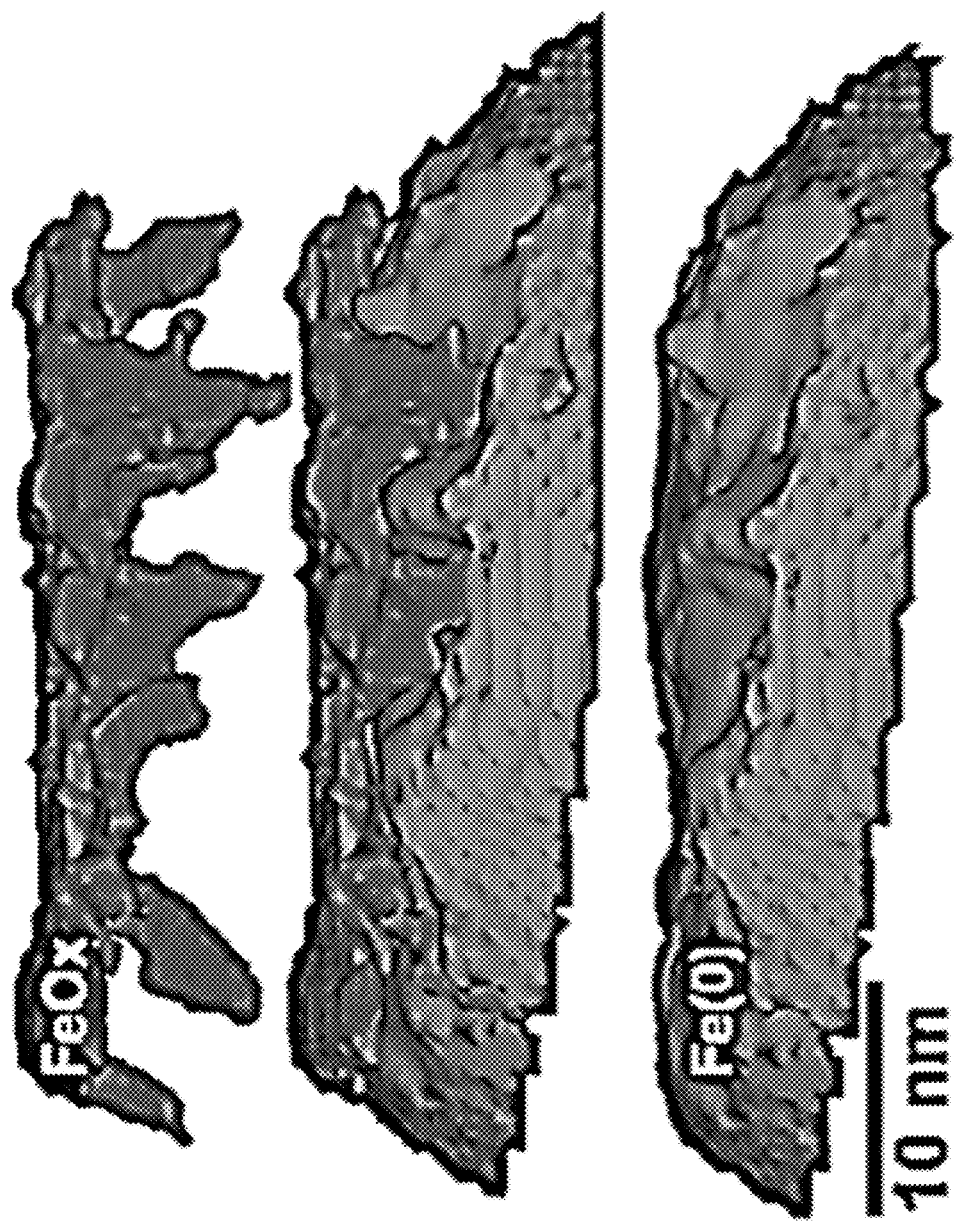
FIGS. 14A-14G: Model of Charge Mobility in a Nano-confined, Insulator-Terminated Metal Conductor.

Zooming out, FIG. 13 offers the following phenomenological interpretation of these findings, followed by a detailed microscopic investigation below. At the pH values used here (5.8 for low- and 8.0 for high-salinity water), the water: oxide interfaces that were investigated are charged. The electrostatic potential reaches not only into the aqueous solution but also into the oxide, depending on the local dielectric properties. Thus, if the oxide nano-overlayer is thin enough, the electrostatic potential extends beyond it to polarize the underlying metal, similar to metal atom charging on ultrathin oxides by underlying metals or the phenomenology of the Cabrera-Mott model. Given the presence of different oxidation states in the iron, vanadium, and nickel oxide nano-overlayers, conduction by intra-oxide electron transfer, like what is known from bulk hematite crystals or from chemical reactions on nanolayer metal-semiconductor heterostructures, is likely to be important as well. Electrical current is then generated by moving an EDL gradient (a "gate") across the metal:metal oxide nanolayer to drive electron transfer within the oxide nano-overlayer, which is coupled to the underlying metal nanolayer. The sharper the gradient, the larger the current density, j. Dendritic iron oxide features of ~5 nm×~10 nm size (FIG. 14A) that extend from the surface into the bulk of the iron metal nanolayer, as revealed by APT, open possibilities for an electron and/or hole ratchet, similar to what has been proposed for low-light energy-driven transducers, or pose limits due to tunneling losses. Structures whose oxide nano-overlayers contain only a single oxidation state, such as those formed from Al or Cr metal, should still produce currents due to contact electrification, but the lack of intra-oxide electron transfer would diminish their current output.

The system presented here differs in several aspects from recent demonstrations of flow-induced power generation. First, the experiments described here are consistent with a mechanism for electrical current generation that involves redox activity in the metal oxide layer. Second, the all-inorganic devices described here are composed of metal nanolayers formed on a given support in a single step over arbitrarily large areas using an electron beam deposition apparatus. Upon exposure to ambient air, an oxide nano-overlayer forms spontaneously and then self-terminates after ~3 to ~5 nm, depending on the thickness of the underlying metal nanolayer. The high purity of the metal nanolayer prevents further growth of the oxide nano-overlayer, resulting in a stable structure. Third, the amphoterism of the thermal oxide nano-overlayer is critical to EDL gradient, or "gate", formation as solutions move across the liquid:solid interface. Fourth, the thickness of the metal nanolayer needed to produce current (FIG. 9C) is comparable to the mean free path of the electrons in it, engendering a propensity for charge motion parallel to as opposed to away from the interface. Fifth, the starting materials, a suitable support, and a standard-purity metal source (Fe, Ni, V, Al, Cr, etc.), are inexpensive.

Figure 14B:
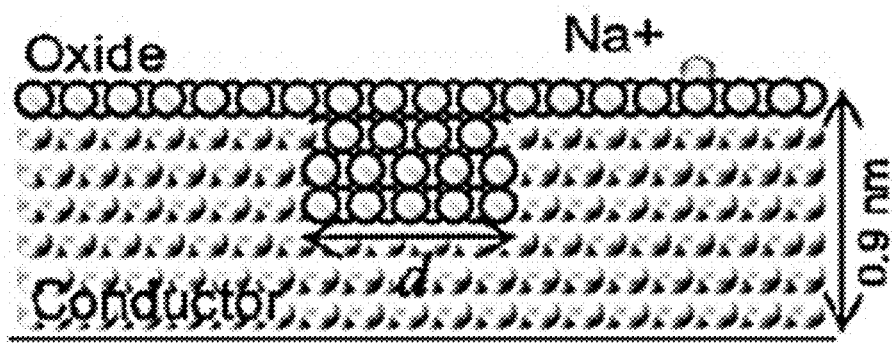
Figure 14C:
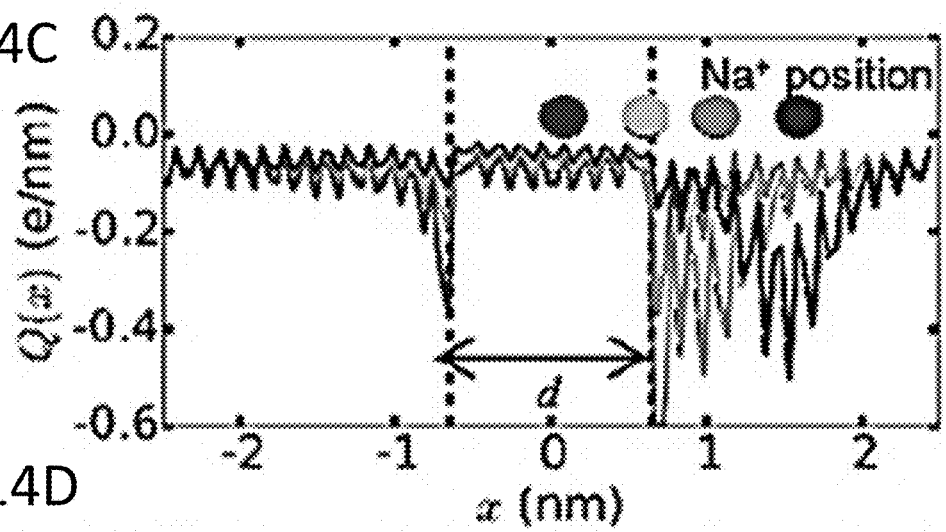
Figure 14D:
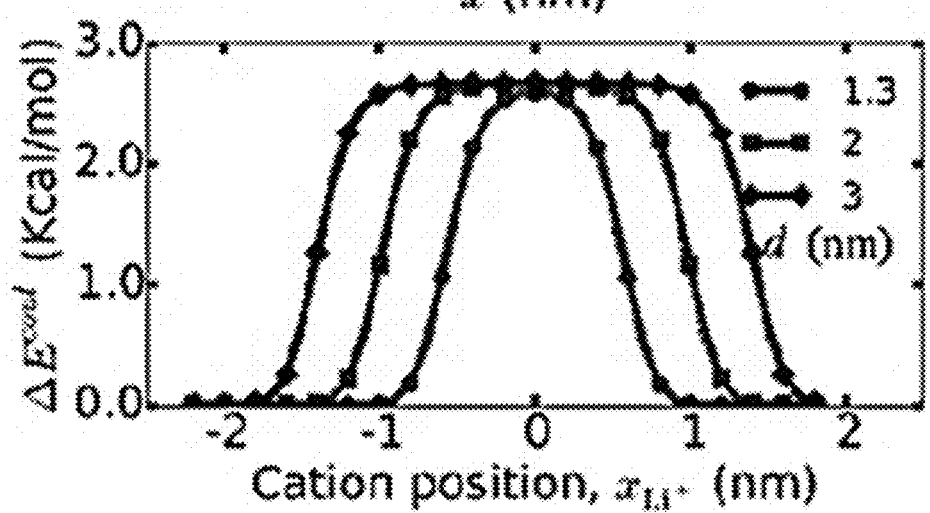

To probe the charge fluctuations in the metal:metal oxide (M:MOx) nanolayer in the presence of moving ions, calculations were performed using an all-atom MD model for the solvent, ions, and a M:MOx nanolayer, including charge-polarization of the nanolayer and image-charge interactions between the nanolayer and the solution. The M:MOx nanolayer is modeled after the APT reconstruction of the Fe:FeOx nanolayer (FIG. 14A) as a polarizable metal conductor (FIG. 14B) with a non-polarizable oxide heterostructure. The subsurface metal/oxide heterostructure is modeled in a simple columnar geometry with a range of values for the width, d. For a given width of the oxide heterostructure (d=1.3 nm), FIG. 14C illustrates the distribution of induced charge in the nanolayer for several positions of a sodium cation. Substantial polarization of the metal for ion positions away from the nonpolarizable heterostructure is reduced when the cation is positioned above the heterostructure (FIG. 14C and FIGS. 15A-15D). This position-dependence of the induced charge manifests in the Coulomb interaction between the ion and the nanolayer (FIG. 14D), leading to a heterostructure-dependent interaction potential between the M:MOx nanolayer and the ion, with a potential energy barrier appearing in the region of the nonpolarizable heterostructure.

Figure 14E:
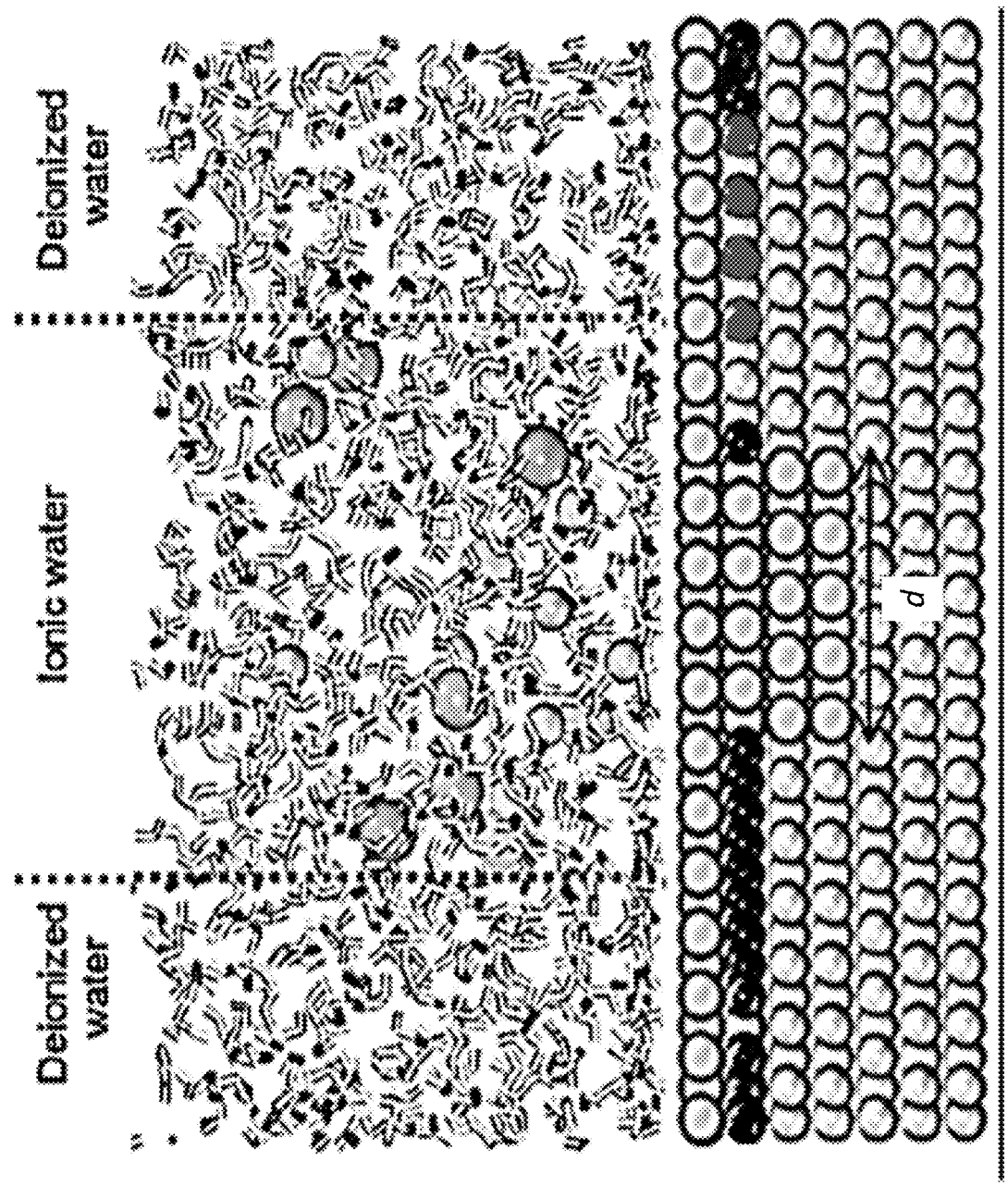
Figure 14F:
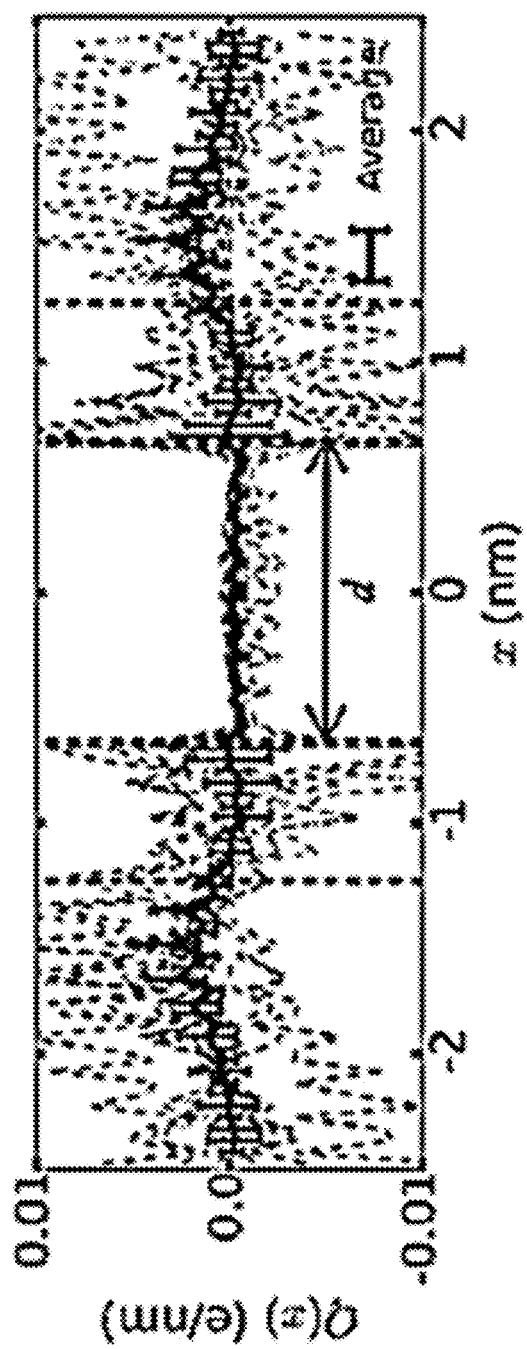
Figure 14G:
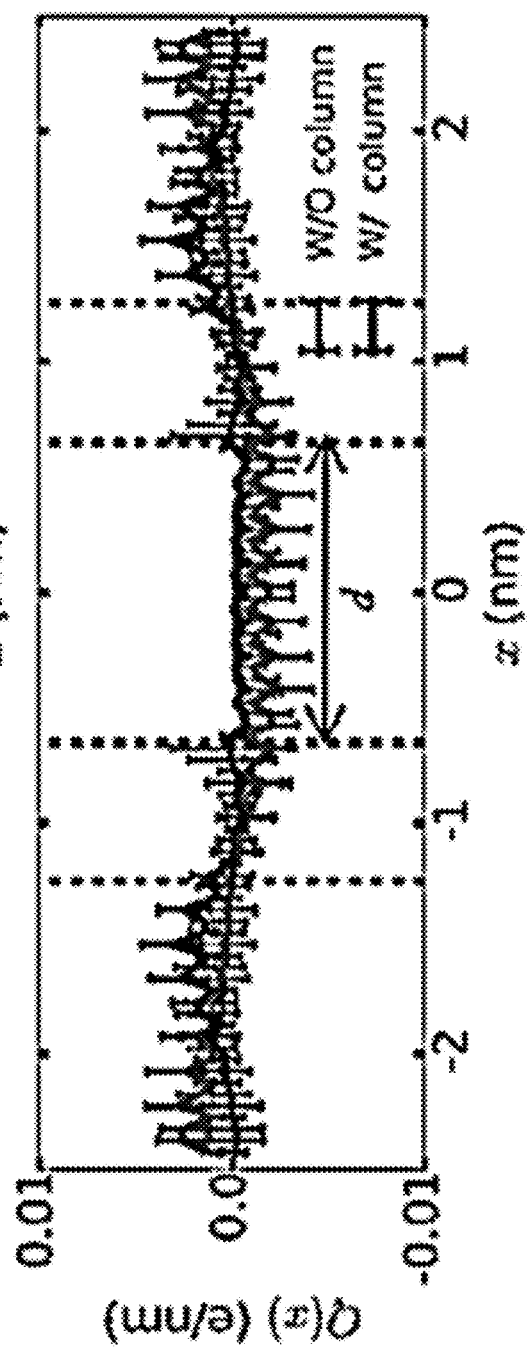

To examine these nanolayer polarization effects in the presence of a solution with alternating salinity, FIG. 14E shows a snapshot of all-atom MD simulations, with vertical lines indicating semipermeable boundaries for the solvated ions and with the instantaneous induced charge fluctuations on the electrode shown in greyscale. FIG. 14F shows the time-averaged charge induced charge distribution for the shown simulation cell, as well as 0.5 ns block-averages of the distribution. Two features are immediately clear: (i) the induced charge distributions in the metal/oxide nanolayer undergo dramatic fluctuations with changes of the ion and water configuration, which reflect changes in the transient electrostatic interactions between the nanolayer and the solvated ions, and (ii) these induced charges are massively damped out in the vicinity of the nonpolarizable heterostructure, i.e., the oxide nano-overlayer. FIG. 14G shows that the effect of the heterostructure on the average induced charge is much smaller than its effect on the fluctuations.

The simulations in FIGS. 14F-14G reveal that the non-polarizable heterostructure model of the metal oxide nano-overlayer creates spatial variation in the local induced charge fluctuations in the metal nanolayer below. These fluctuations are proportional to the local interfacial capacitance, i.e., $C_F = \beta \langle (\delta Q(x))^2 \rangle$. Given that this interfacial capacitance connects droplet motion to induced current, $$I = -\psi \frac{dC_F}{dt}$$

where $\psi$ is the surface potential, the simulations thus provide a direct connection between the morphology of the oxide heterostructure and the gate-induced current presented here. Moreover, these simulations reveal that the interfacial capacitance that gives rise to the current is strikingly sensitive to the electronic character and spatial features of oxide heterostructure, such that nanometer-scale changes in the heterostructure give rise to unexpectedly large effects in the resulting interfacial capacitance.

The effects observed in the simulations are expected to be further enriched by the amphoterism of the oxide overlayer, which is important for determining the sign and magnitude of the charge and potential distributions within the EDL under conditions of varying aqueous pH and ionic strength. Control over the structure of the oxide dendrites, their number density, and their width and depth offers the possibility to further optimize charge mobility along the potential hotspots on the dendrites and minimize possible leakage due to tunneling. Additional control comes from the choice and concentration of ions in the aqueous phase and the steepness of the salt concentration gradient, which determines the area of the gate footprint at the aqueous/solid interface (steeper gradients lead to increased current densities, j). Moreover, the volcano plot-like current vs. M:MOx film thickness data shown in FIG. 9C suggests that film thickness on the order of the mean free path of the electron is desirable for current generation, offering an additional means of optimizing the electron current flow.

Figure 16:
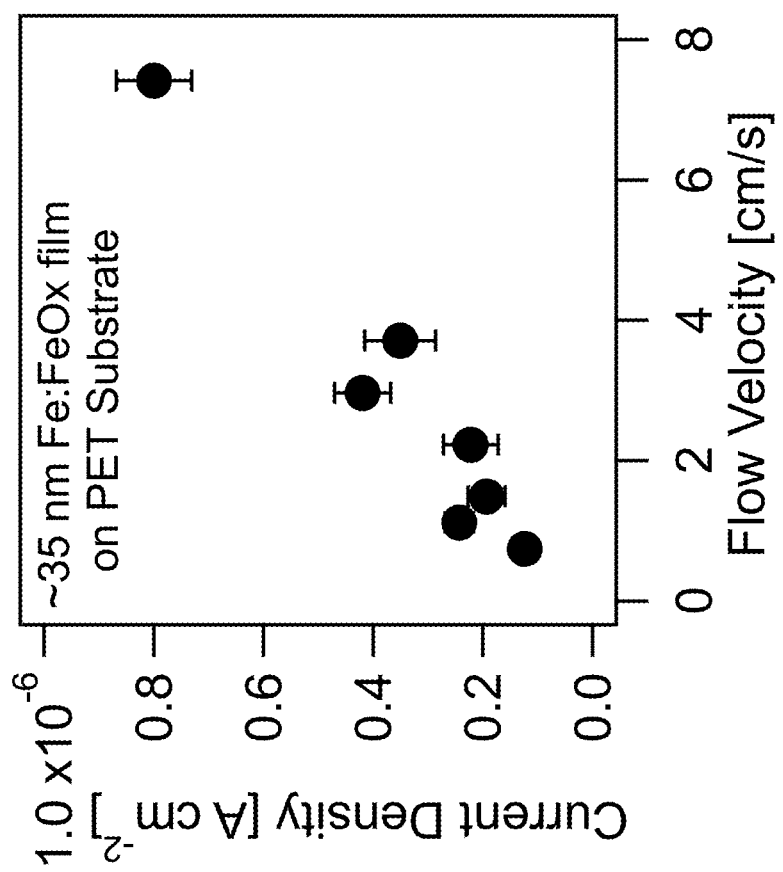
FIG. 16 depicts current density vs. flow velocity for a ca. 35 nm thin Fe:FeOx nanmolayer on a poly(ethylene) terephthalate (PET) substrate obtained when alternating DI water and 1 M NaCl solution segments every 20 sec.

The relatively modest flow velocities surveyed here (a few cm s$^{-1}$) indicate the approach presented here may work in entirely passively operating assemblies, yet there is ample room for improvement. The use of appropriate metals having biocidic properties (Al, Zn, Ag, Cu) may have the additional benefit of counteracting biofilm formation in the field. The optical properties of the iron and nickel nanolayers also open the possibility of further charge carrier generation by visible light, conversion boosting of solar cells, or the coating of building windows with the nanolayers, given the ionic strength of rainwater (0.2 mM) and the low absorbance of the nanolayers in the visible spectrum. PVD onto plastics or flexible substrates (FIG. 16) also allows for large-area yet light-weight and/or foldable designs. PVD of appropriately formulated metal nanolayers into tubes allows for implantable applications in vivo, while PVD of metal nanolayers onto a range of other polymers surveyed opens the door to transducers operating in three-dimensional structures prepared, for instance, by 3D printing.

A plurality of the devices described herein could be connected for increased power generation. By way of example, a set of 100 connected devices of 10 m$^2$ area could be connected to generate 2 kW hours, or more, using an ionic solution with temporally varying the salinity at 10 Hz. This estimate is based on measured observations of approximately 30 microWatt g$^{-1}$ water m$^{-2}$ per salinity alternating event according to an external load resistance of 100 kOhm.

Methods.

Figures 17A, 17B:
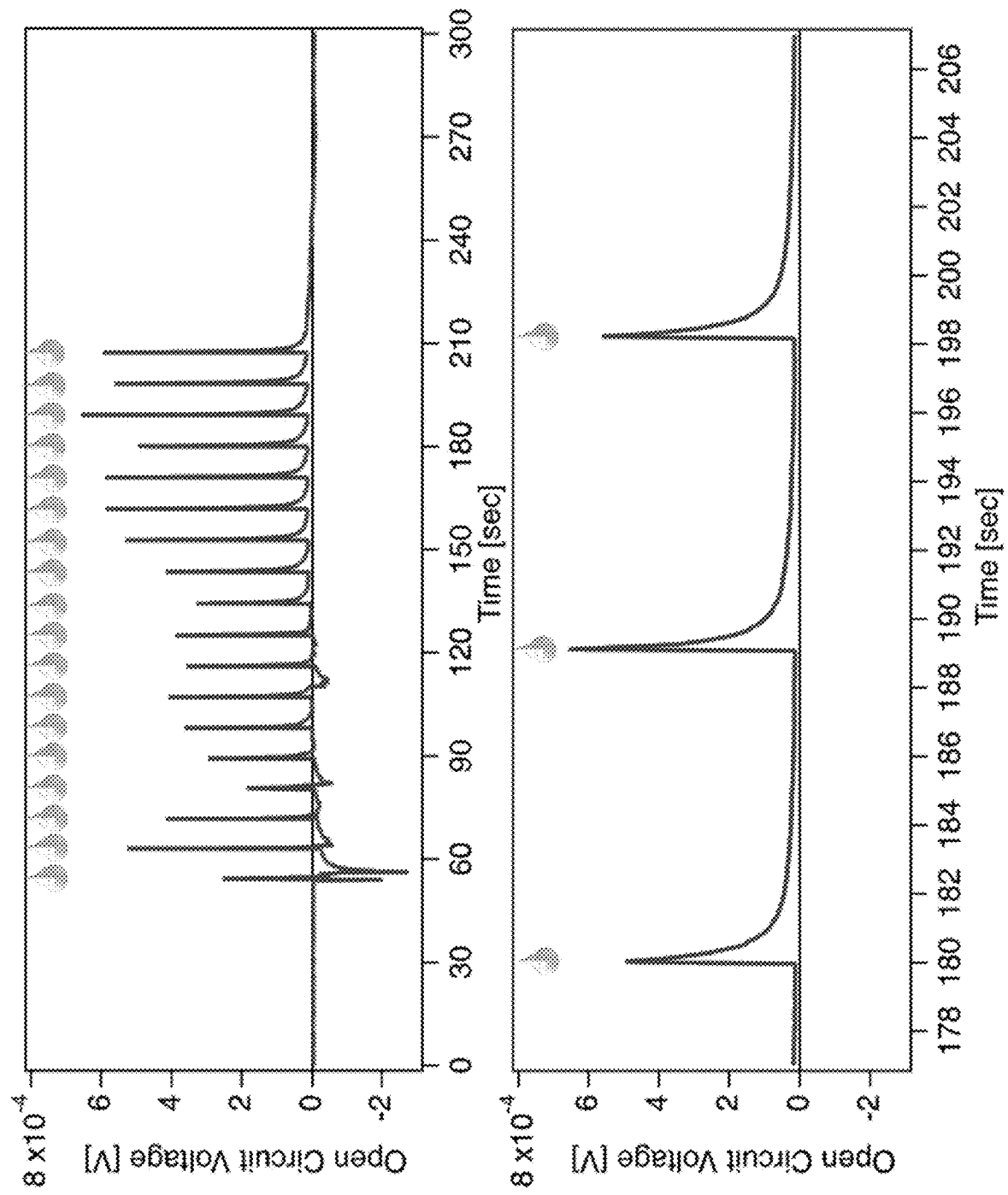
FIGS. 17A-17B depicts OCV measured for a freshly prepared 10 nm thin iron nanofilm using 100 mM salt and a drop rate of 0.5 mL/min (FIG. 17A) and zoomed in to show three voltage spike events (FIG. 17B).

The nm-thin iron layers and their oxide nano-overlayers were prepared on glass microscope slides (VWR) and characterized as described in previous work. (Faurie-Wisniewski, D., et al., *The Journal of Physical Chemistry C* 118, 23256-23263 (2014); and Boamah, M. D. et al., arxiv: 1809.04909 (2018).) Computer controlled multi-channel Ismatec peristaltic pumps (ISM4408) were used. Aqueous solutions were prepared from NaCl (Sigma-Aldrich) in Millipore water adjusted to pH 7 or equilibrated with ambient air to pH 5.8 and containing various amounts of NaCl, as indicated in the Brief Description of the Drawings. "Instant Ocean Aquarium Sea Salt" was used as received from Amazon (ASIN: B00NQH210G). The drop experiments were performed using motorized syringe pumps (Harvard Apparatus Elite 11). Using Teflon tubing, drops having an average volume of 0.0165 (1) mL (measured for a flow rate of 0.5 mL/min) were released in ambient laboratory air from a height of 10 cm onto a given device held in air by an electrically insulated clamp at an incident angle of ~20 degrees. Variations in incident angle, drop release height, and drop size led to variations in drop flow dynamics and velocity on the nanolayer surfaces and corresponding variations in magnitude and duration of the measured open circuit voltage spikes, similar to what had been reported in the earlier studies using carbon- and semiconductor structures that are mentioned above. Nanolayers stored for prolonged periods of time (~two years) in ambient laboratory air showed larger contact angles (Computerized First Ten Angstroms contact angle goniometer, θ=57±5° from seven replicates using DI water) than freshly prepared nanolayers (θ=37±3° from seven replicates using DI water), on which the water drops spread considerably more while also producing open circuit potential spikes that are somewhat larger in magnitude and longer in duration (FIGS. 17A-17B). Given the potential relevance of the system described here for use in the ambient environment, the results from nanolayers that had been stored in the dark for about two years in conical centrifuge tubes made of polypropylene (Falcon, 50 mL, with screw top) containing ambient air are emphasized here. Drops rolling off the device were collected in a receptacle. Open circuit potential measurements were performed using a Keithley 2100 voltmeter and standard alligator clip-on probes, taking special care to keep the probes dry. The resistance of the dry nanolayers was around 50 to 500 Ohm (Keithley 2100), depending on layer thickness. Short circuit current measurements were carried out on an Agilent B1500A semiconductor parameter analyzer equipped with a high-resolution SMU and on a Keithley 6485 Ammeter.

XPS. XPS depth profile measurements were carried out with a Thermo Scientific ESCALAB 250 Xii instrument stationed at the NUANCE center at Northwestern University. The instrument is calibrated to the Au $4f_{7/2}$ line at 83.96 eV. It uses a Kα radiation from a monochromatic aluminum source. A flood gun is used for the ejection of low energy $Ar^+$ ions and electrons to compensate for surface charging. The 2 mm raster size 2 keV etching mode ion ($Ar^+$) gun at mid current was employed to prevent the reduction of trivalent ions to divalent ions.

The results are shown in FIGS. 12A-12E. The physical-vapor deposited aluminum nanolayers show Al(III) species in the oxide nano-overlayer, and the bulk is Al(0). For chromium nanolayers, XPS peaks indicate the presence of Cr(III) oxides in the oxide overlayer, and the bulk is Cr(0). Iron nanolayers were characterized with Raman spectroscopy, XRD, APT, and XPS in recent publications. (Boamah, M. D. et al., The *Journal of Physical Chemistry C* 122, 28225-28232 (2018); and Faurie-Wisniewski, D. et al., *The Journal of Physical Chemistry C* 118, 23256-23263 (2014).) Iron nanolayers have nano-overlayers containing magnetite and hematite, protecting the Fe(0) bulk. XPS peaks of nickel nanolayers indicate the presence of both Ni(III) and Ni(II) oxides on the surface, while the bulk is Ni(0). For vanadium, V(V)/(IV) oxides are on the surface, while the bulk is V(0).

Computational Methods.

Molecular dynamics simulations were performed using a polarizable model for the conductive regions of the iron nanolayer. In these simulations, possible redox activity in the oxide layer was not accounted for; instead, it was simply modeled as an insulator. The atoms in the nanolayer were fixed in the face-centered cubic structure with a lattice parameter of 0.392 nm and a (111) termination at the interface. The orthorhombic simulation cell was oriented such that the z coordinate was perpendicular to the nanolayer surface, the x coordinate coincided with the direction of the gate motion, and the simulation cell was periodically replicated only in the x and y coordinates. In all simulations, the length of the simulation cell in the x and y coordinates was 4.979 nm and 4.791 nm, respectively, such that the nanolayer was described using seven layers of atoms, with each nanolayer layer containing 360 atoms (for a total of 2520 nanolayer atoms). Atoms in the nanolayer were modeled as being either oxide-like (i.e., non-polarizable) or metallic (i.e., perfectly conductive). In all simulations, the top layer of atoms in the nanolayer was assumed to be oxide-like, and the arrangement of oxide-like atoms below the nanolayer surface was varied to model the subsurface heterostructure, as described.

Interactions between atoms in the nanolayer and other atoms in the simulation cell are described using both electrostatic and Lennard-Jones (LJ) interactions. Oxide-like atoms in the nanolayer were uncharged, while the charges of the metallic atoms of the nanolayer were allowed to fluctuate in response to charges in the solution. The metallic portion of the nanolayer was modeled as one of two fixed-potential electrodes with zero potential bias, with the fluctuating charge distribution in the metallic portion of the nanolayer described in terms of a sum of atom-centered spherical Gaussian functions, $$Q_i(r, t) = A_i(t) * \left(\frac{\eta^2}{\pi}\right)^{3/2} \exp[-\eta^2(r - R_i)], \quad \text{Eqn. S1}$$

of width $\eta=19.79$ $nm^{-1}$ and amplitude $A_i(t)$ that was determined using an extended Lagrangian method. (J. I. Siepmann et al., *J. Chem. Phys.* 102 (1995).) Although all calculations involving the iron nanolayer focused on a single solid/liquid interface, the fixed-potential electrode simulation model required that two electrodes be included in the simulation cell; the second polarizable electrode was simply placed a large distance from the interface of interest, separated by ~10 nm of vacuum in the z coordinate. All simulations were performed using the LAMMPS software package. (S. Plimpton, *J. Comp. Phys.* 117, 1-19 (1995).)

Nanolayer/Liquid Interface MD Simulations.

Simulations of aqueous solutions in contact with the nanolayer were performed using SPC/E water and NaCl ions. (H. J. C. Berendsen et al., *J. Phys. Chem.* 91 (1987); and D. E. Smith, et al., *J. Chem. Phys.* 100 (1994).) LJ parameters for the Na+, Cl−, and nanolayer atoms are provided in Table 1. The cross terms were obtained using Lorentz-Berthelot mixing rule. The LJ interactions and the real-space part of the Coulomb interactions were truncated at 0.98 nm; the long-range contribution of Coulomb interaction was treated by the particle-particle particle-mesh method. (R. W. Hockney, et al., Raylor & Francis, New York, N.Y., 1989.) Via these LJ interactions, the oxide surface preferentially interacts with the $Na^+$ cations over the $Cl^-$ anions.

TABLE 1

Lennard-Jones parameters for water, ions, and nanolayer atom.

| | σ (nm) | ε (kcal/mol) |
|---|---|---|
| $Na^+$ | 0.235 | 0.13 |
| $Cl^-$ | 0.44 | 0.1 |
| O (SPC/E water) | 0.3166 | 0.1554 |
| Nanolayer atom | 0.2534 | 0.078 |

To enforce the regions of alternating salinity in the solution (FIG. 13), semipermeable boundaries are introduced to interact only with the NaCl ions; the boundaries are positioned at x=1.25 nm and x=−1.25 nm in the simulation cell, and they interact only with the salt ions via a truncated LJ potential with epsilon=10 kcal/mol and sigma=cutoff=0.1 nm. Simulations of the solution/nanolayer were initialized with a slab of water/ions in contact with the nanolayer; after a short period of equilibration, the outermost layer (furthest from the nanolayer) was frozen in space to provide a fixed, amorphous boundary between the solution region and the vacuum of the remaining simulation cell. Finally, the distance between this fixed layer of water molecules and the position of the nanolayer was adjusted so that the pressure of the confined solution was 1 atm, and it was confirmed that the osmotic pressure introduced by the semipermeable boundaries did not significantly alter the density of water in the ionized vs. deionized solution regions. The final thickness of water along the confinement was ~3 nm.

The classical molecular dynamics equations of motion were evolved using the velocity Verlet integrator with a timestep of 2 fs; rigid-body constraints for the water molecules were enforced using the SHAKE algorithm. (J.-P. Ryckaert et al., *J. Comp. Phys.* 23 (1977).) The simulations were performed at a temperature of 298.15 K, enforced via the Nose-Hoover thermostat with a damping timescale of 100 timesteps.

Figure 18:
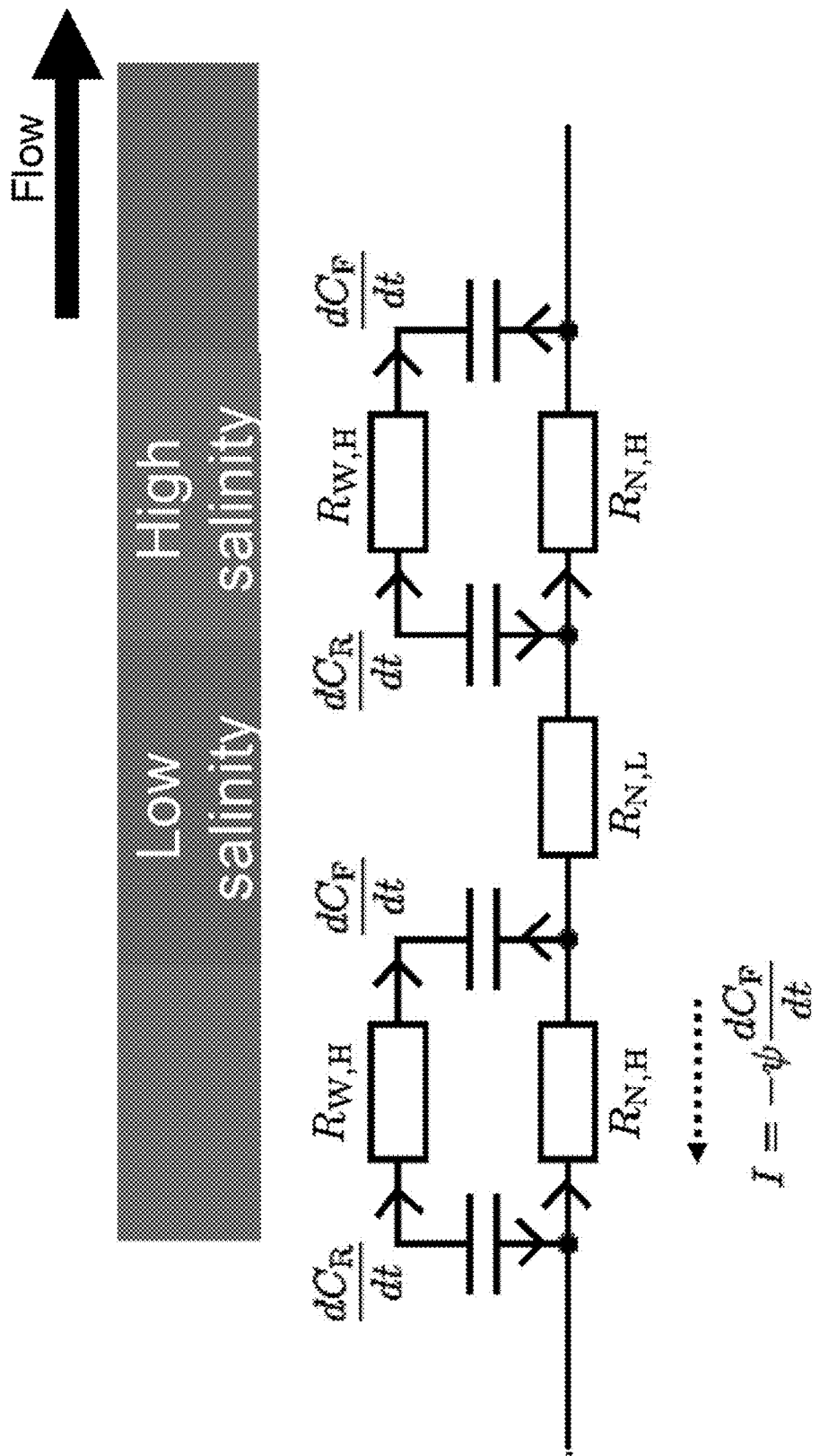
FIG. 18 depicts an equivalent circuit for the current induced in the system of liquid flow across the nanolayer with alternating high- and low-salinity segments. At the top, the alternating salinity of the liquid and flow direction are indicated. The liquid resistance to ion flow at low and high salinity are indicated by $R_{W,L}$ and $R_{W,H}$, respectively. The resistance to electron flow in the contact area between the nanolayer and water at low and high salinity are indicated by $R_{N,L}$ and $R_{N,H}$, respectively. The interfacial capacitance at the front and rear salinity boundaries ($C_F$ and $C_R$, respectively), which include contributions from the redox activity of the semiconducting metal oxide layer.

FIG. 18 presents the equivalent circuit for the current induced in the system of liquid flow across the nanolayer with alternating high- and low-salinity segments. The leftward electrical current in the nanofilm is generated by the relative motion of the ions (adsorption or desorption) that form the electrical double layer as the salinity gradient boundaries move.

FIG. 18 is closely related to the equivalent circuit presented for droplet motion on graphene in J. Yin et al., *Nature Nanotechnology* 9, 378-383 (2014), with two key distinctions. First, the current case is for liquid flow with alternating salinity. Second (and more important), the interfacial capacitance in the system presented here includes contributions from both the image charge formation in the metal layer as well as the large effect of electron transfer within the semiconducting metal oxide layer of the nanofilm surfaces.

Example 2

Figure 19:
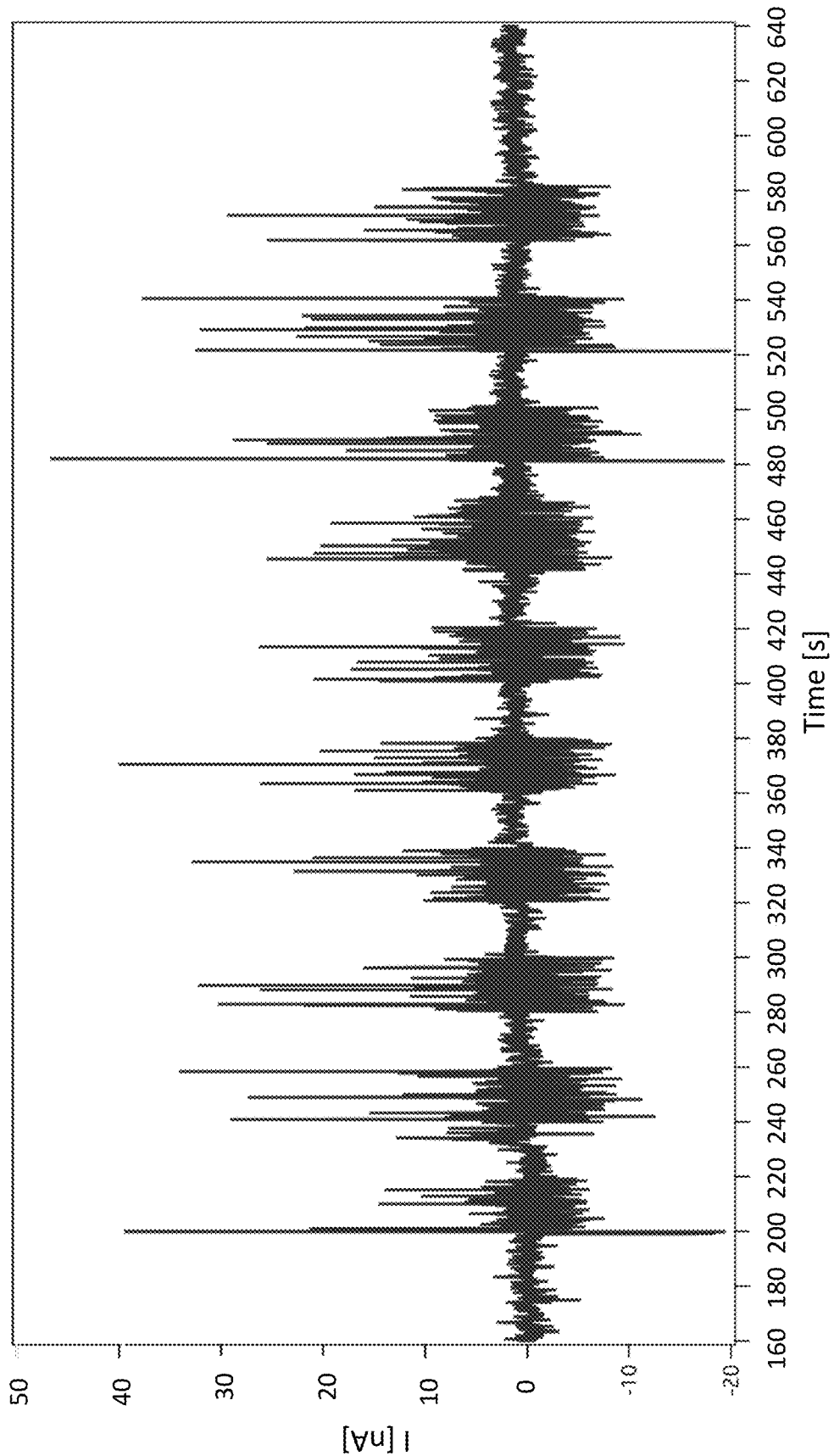
FIG. 19. Bunched current production recorded while flowing an aqueous solution of $YCl_3$ over a 10 nm thin iron nanolayer at a flow rate of 100 mL min' using start-stop flow.

This example illustrates a device that uses stop-flow operation to generate a time-varying current. An iron film having a thickness of 10 nm was used as the metal layer. An iron oxide overlayer formed spontaneously on the surface of the iron layer in air to a thickness of a few nm, as determined by XPS spectroscopy. An aqueous solution of $YCl_3$ was flowed over the amphoteric iron oxide that formed on the iron film at a flow rate of 100 mL/min for 20 seconds, followed by a 20 second pause in the flow, and then the resumption of the flow. As shown in FIG. 19, this generated in a time-varying current with an on-off pattern.

Example 3

Figure 20:
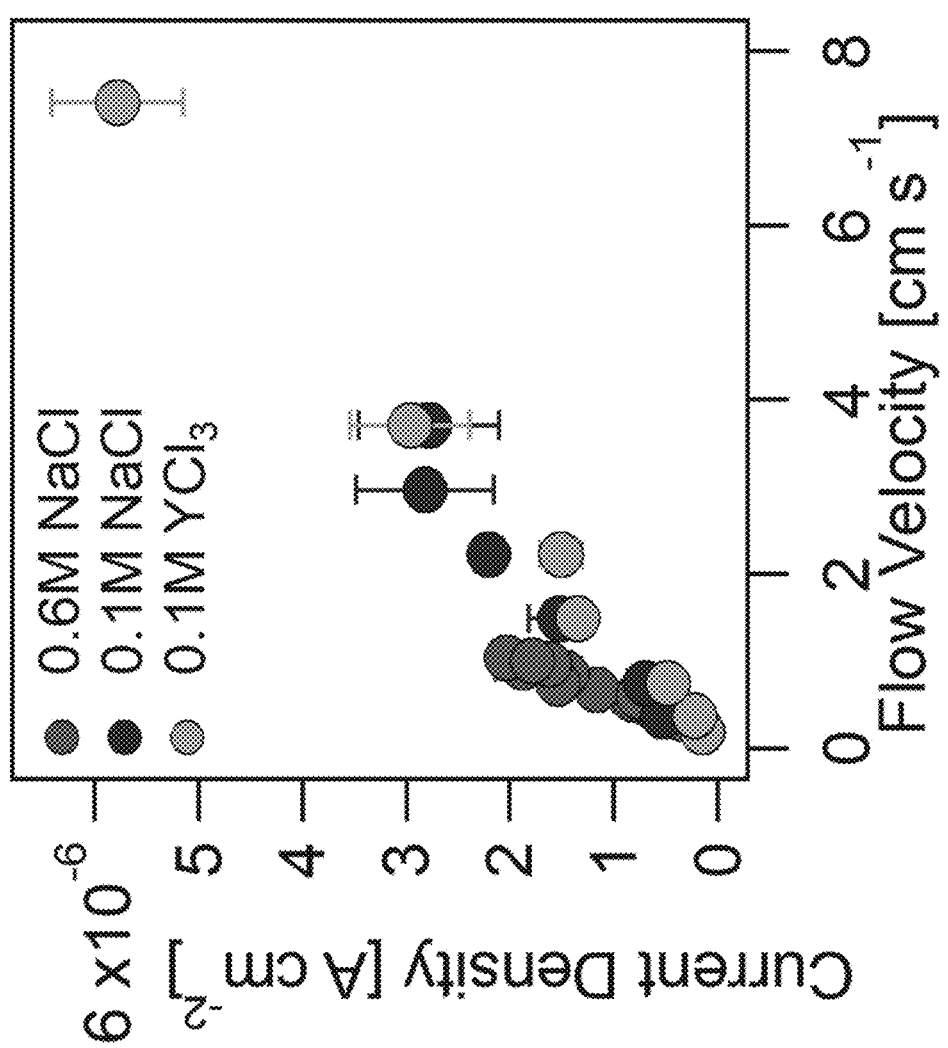
FIG. 20. Current produced using a 10 nm iron nanolayer when using a flow that alternated a 0.1 M aqueous solution of NaCl and $YCl_3$ with deionized water at various flow velocities.

This example illustrates the use of an ionic solution that contains multivalent ions in the generation of an electronic current. An iron film having a thickness of 10 nm was used as the metal layer. An iron oxide overlayer formed spontaneously on the surface of the iron layer in air to a thickness of a few nm, as determined by XPS spectroscopy. Ionic solutions of the salt $YCl_3$ (0.1 M) in DI water were used. Ionic solutions of NaCl (0.1 M and 0.6 M) in DI water were used for comparison. Solutions of both salts produced a current in the iron layer when the salt solutions were flowed over the metal oxide surfaces over a range of flow rates, as shown in FIG. 20. These results demonstrate that mixtures of electrolytes comprised of a variety of different ions can be customized to serve the need of specific application endpoints.

Example 4

This example illustrates the utilization of a device as a pump by operating the device in reverse. A nickel film having a thickness of 20 nm coated onto a glass slide was used as the metal layer. A nickel oxide overlayer formed spontaneously on the surface of the nickel layer in air to a thickness of a few nm, as determined by XPS spectroscopy. A drop of 0.1 M salt solution was placed onto the surface of the nickel oxide tilted glass while the slide was in a tilted position. Applying a voltage across the salt solution resulted in the drop moving up the surface of nickel oxide, against gravity, indicating the device is doing work. Drops of deionized water showed no discernable movement when a voltage was applied in the same manner. This demonstrates that the device can be used as a silent and frictionless pump with no moving parts to move bodies of ionic solutions, including ocean water, bodily fluids (e.g., blood), or brines across a static surface.

Example 5

This example illustrates the use of wave action to generate a varying current/voltage in a metal film. A nickel film having a thickness of 20 nm coated onto a glass slide was used as the metal layer. A nickel oxide overlayer formed spontaneously on the surface of the nickel layer in air to a thickness of a few nm, as determined by XPS spectroscopy. In order to simulate the exposure of the nickel oxide surface to repeated wave action, the beaker of 0.6 M NaCl solution held in a beaker was repeatedly moved up and down over the surface of the stationary nickel oxide film while the glass slide was held vertically. As shown in FIG. 21A and FIG. 21B, this resulted in the regular, repeated wetting and dewetting of the metal oxide and resulted in a varying current and voltage in the nickel layer.

Example 6

This example further illustrates the use of wave action to generate a varying current/voltage in a metal film. A nickel film having a thickness of 10 nm coated onto a 3" by 1" glass slide was used as the metal layer. A nickel oxide overlayer formed spontaneously on the surface of the nickel layer in air to a thickness of a few nm. In order to simulate the exposure of the nickel oxide surface to repeated wave action, the slide was partially immersed in a wavetank containing Instant Ocean (FIG. 22A) and the current output per wave was measured (FIG. 22B). Notably, after 9 days in the wavetank, the nickel film did not delaminate or corrode and the current output was unchanged (FIG. 22C).

Example 7

This example illustrates the use of a magnetic support to enhance the wave action-induced current density output of a nickel film having a nickel overlayer.

Figure 23A:
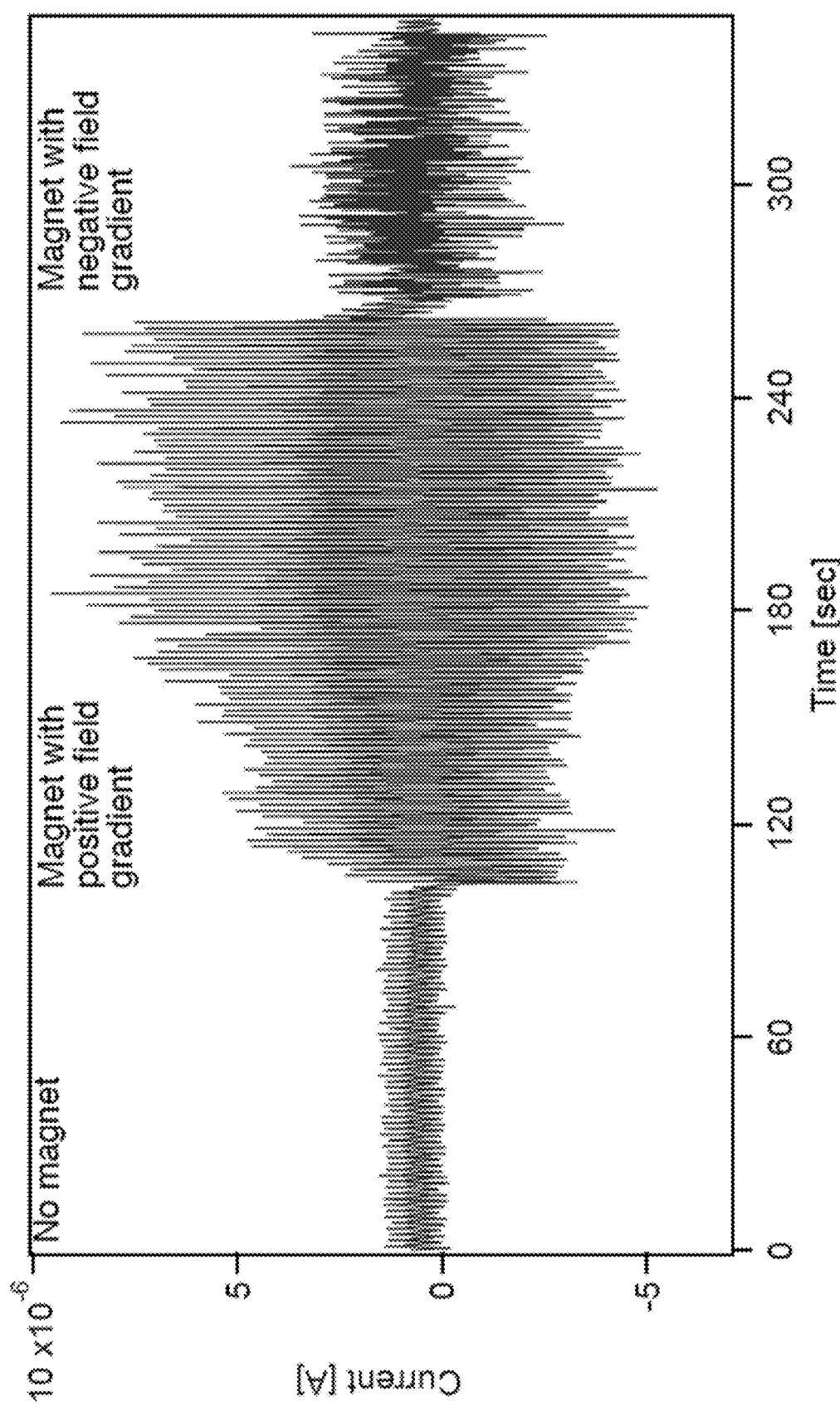
FIGS. 23A, 23B, and 23C. Effect of magnetic field on the wave action-induced current output of an iron film having an iron oxide overlayer (FIG. 23A). Effect of the sign of the magnetic field gradient on current output for the iron film having an iron oxide overlayer (FIG. 23B). Effect of surface flux density on current output for the iron film having an iron oxide overlayer (FIG. 23C).

2" by 1" square wetted areas of either a 10 nm thin iron or nickel nanolayer were deposited on a 3×1 inch microscope glass slide placed in a 55-gallon wavetank filled with Instant Ocean, and a 0.5 Hz wave action was induced. In the absence of a magnet, the iron layer and its oxidized overlayer produced a current output of approximately two microampere, as shown for times 60 seconds to about 100 seconds in FIG. 23A. However, when the south face of a neodymium bar magnet (N52 grade, 60 mm length×10 mm width×5 mm thickness) having a flux density gradient of 2000 Gauss over the 60 mm length of the bar (4000 Gauss on the one end of the bar, 2000 gauss on the other end) was pressed against the glass support opposite the iron film, the current density was increased by a factor of six (FIG. 23A, approximately 100 seconds to 260 seconds, and FIG. 23B). Reversing the gradient direction reduced the enhancement considerably, but still produced a modestly enhanced four microampere output (FIG. 23A, approximately 260 seconds to approximately 350 seconds, and FIG. 23B). A control experiment using a 10-nm thin aluminum nanolayer produced no current enhancement in the presence of a magnetic field.

Figure 23C:
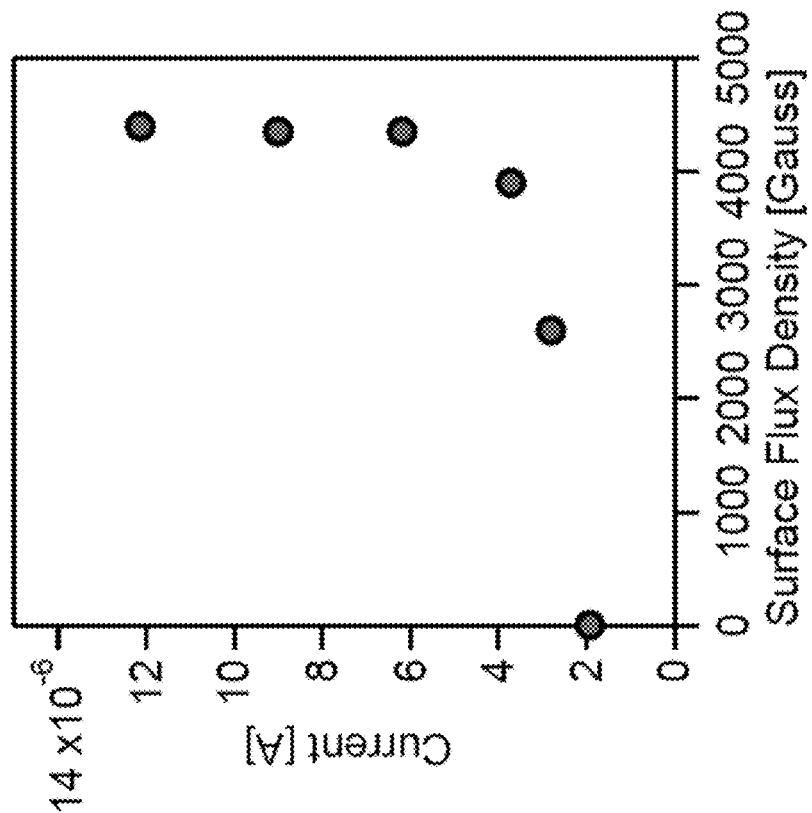
Figure 23B:
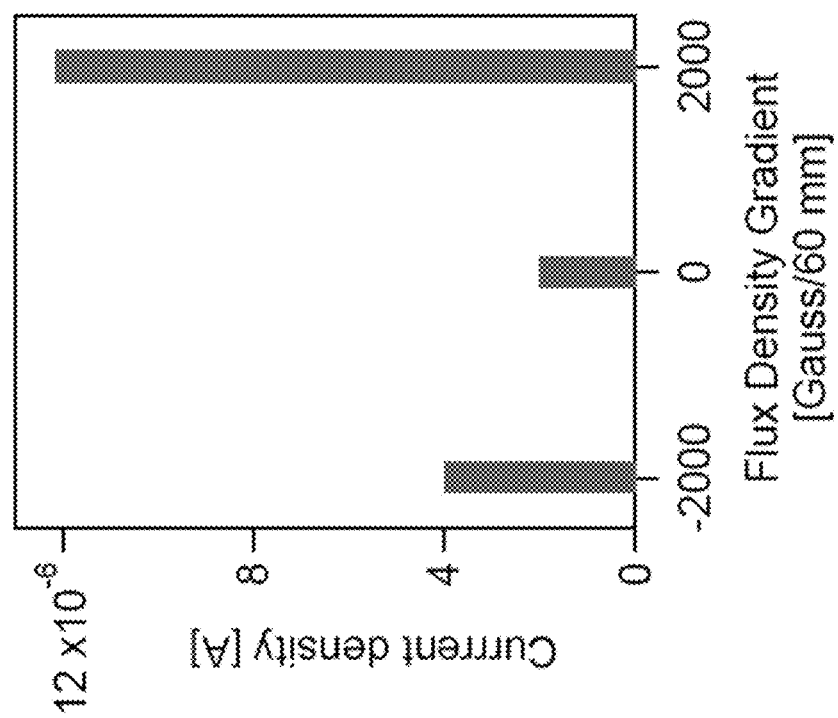

The current enhancement was strongly non-linearly related to the surface flux density, as shown in the graph of FIG. 23C.

Example 8

In this example, nanolayers having a thickness of ten nm were subjected to wave action in a tank filled with Instant Ocean operating at approximately 0.5 Hz with a wave height velocity of 5 cm sec$^{-1}$. With a wetted area of 2×2.5 cm$^2$, peak-to-peak currents (resp. voltages) of around 1 μA (resp. 50 μV) produced during each wave event were increased to 50 μA and 5 mV when bracket-shaped neodymium N52-grade permanent magnets having flux density gradients of about 0.1 T cm$^{-1}$ were brought into contact with nickel nanolayers, chosen for their demonstrated propensity to resist corrosion and delamination. The magnets were shown to amplify modest effects obtained from plain glass slides (no metal nanolayers present, ~0.5 nW maximum peak power per wave event) by a factor of ~500 in maximum peak power when the glass slides were coated with 10 nm nickel nanolayers (~0.25 μW per wave event at the same wetted area). The magnets themselves showed no current or voltage production with wave action. Given the devices operate in series and parallel, as demonstrated using 10-nm iron nanolayers, opportunities exist to design high total internal surface area structures having footprints commensurate with open ocean operation.

Figure 22A:
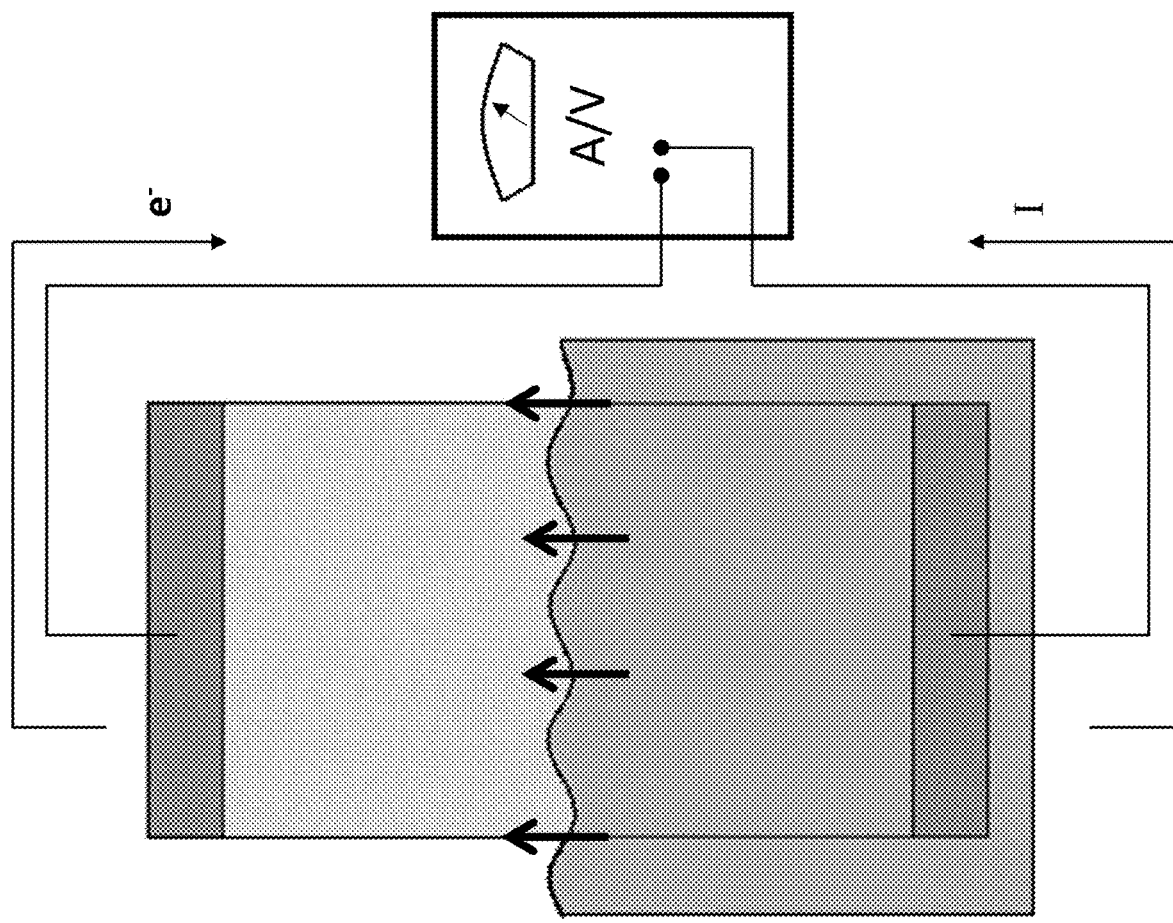
FIGS. 22A, 22B, and 22C. Illustration of a nickel-coated glass slide in a wavetank (FIG. 22A), the measured current output per wave (FIG. 22B), and the current output over the course of 9 days in the wavetank (FIG. 22C).
Figure 22C:
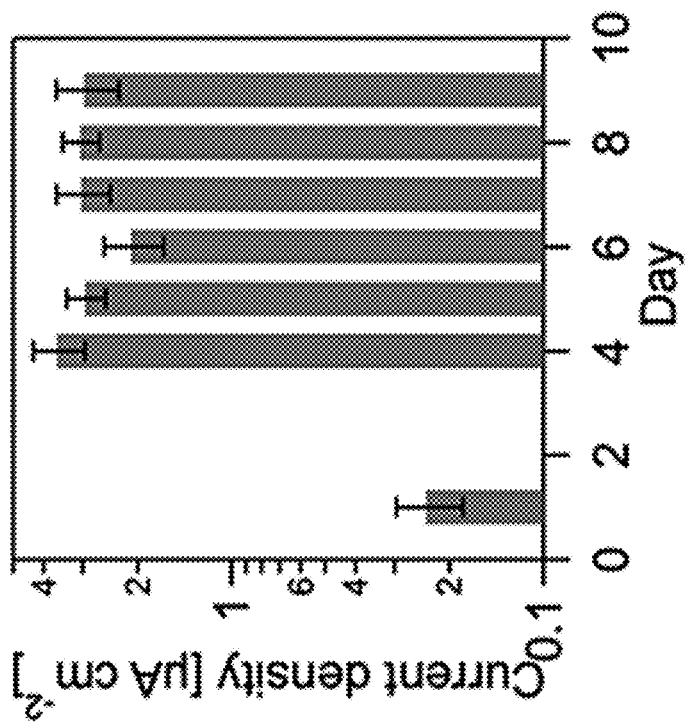
Figure 22B:
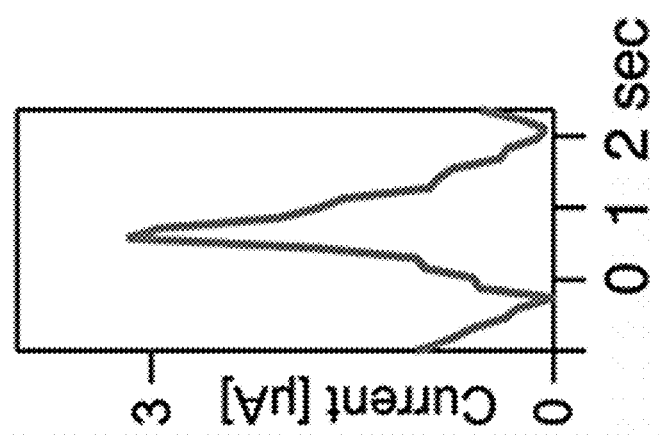

The metal nanolayers were then operated in an electrically grounded 210-liter wavetank half-filled with Instant Ocean water (FIG. 22A). Two slides were paired back to back, each coated on one side with a 10 nm nickel nanolayer so that the moving water contacted only the metal nanolayers with the total wetted area being two times 2.5×5 cm$^2$. This approach minimized the contribution of contact electrification on the bare glass side and allowed energy transduction to be probed from the metal nanolayers only. The nanolayers did not corrode or delaminate during operation in the wavetank for over a week, which was attributed to the chemical purity of the metal nanolayers as determined by X-ray photoelectron spectroscopy (XPS) and atom probe tomography (APT), as well as the well-known corrosion resistance of nickel to salt solutions.

Figure 24:
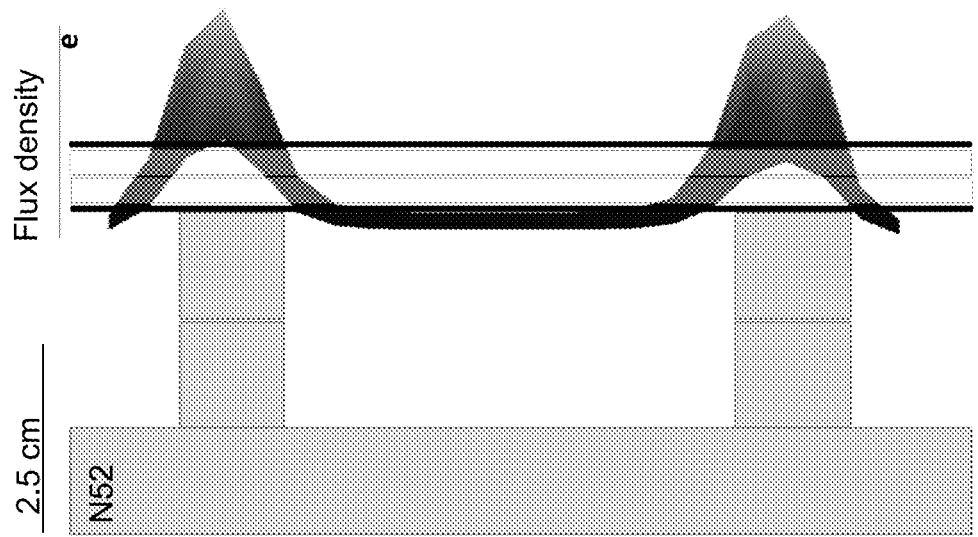
FIG. 24. Bracket-shaped magnet having up to 0.64 Tesla at each pointed end and around 0.05 T in the center (center, dark grey=0 T, light grey=0.64 T).
Figures 25A, 25B:
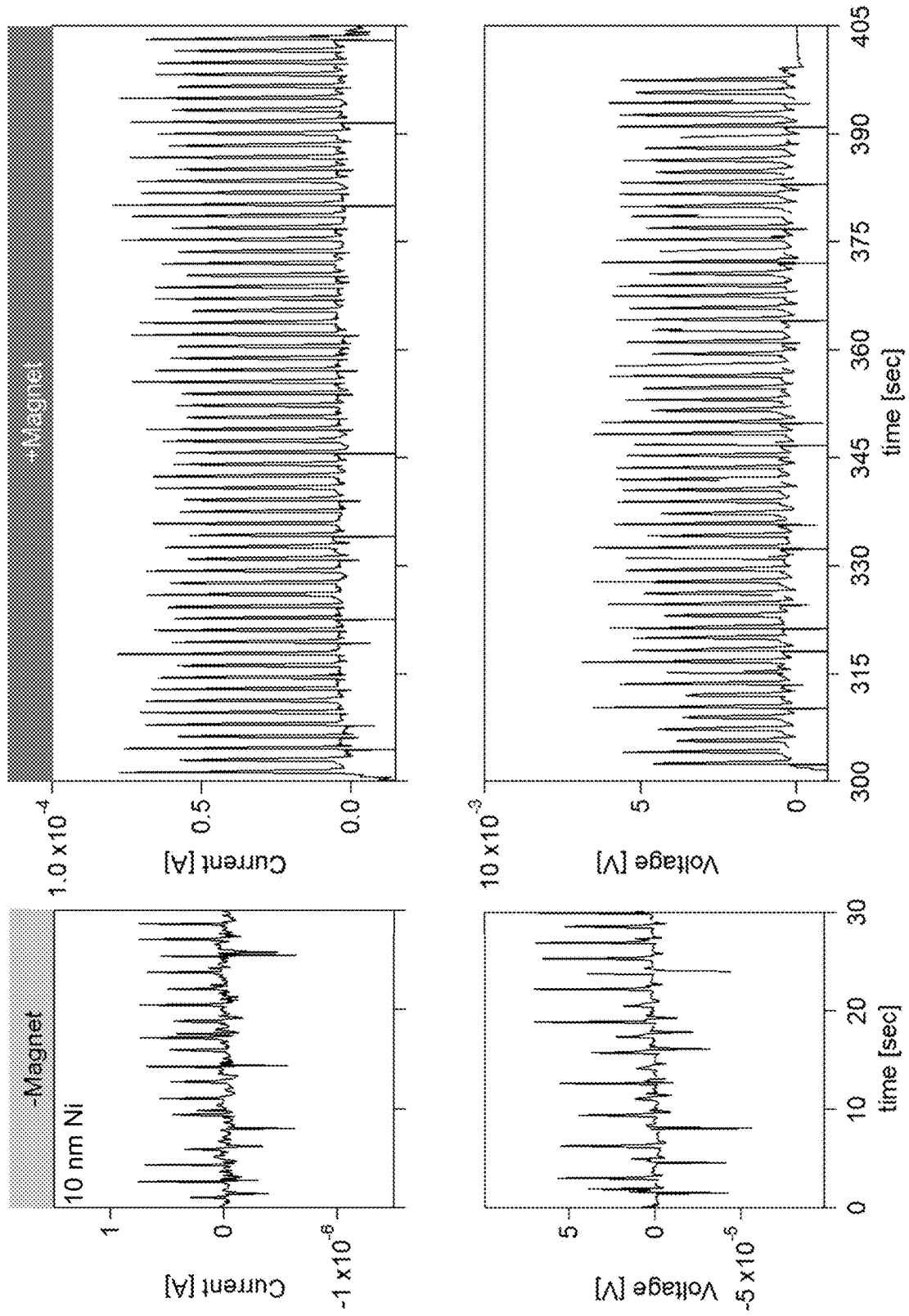
FIGS. 25A and 25B. Current and voltage enhancement by a [-shaped N52-grade magnet. Current (top) and voltage (bottom) measured as a function of time during wave action without (FIG. 25A) and with (FIG. 25B) magnet. The contact area for the magnet and the nanolayer is 2.5×0.6 mm.
Figure 26:
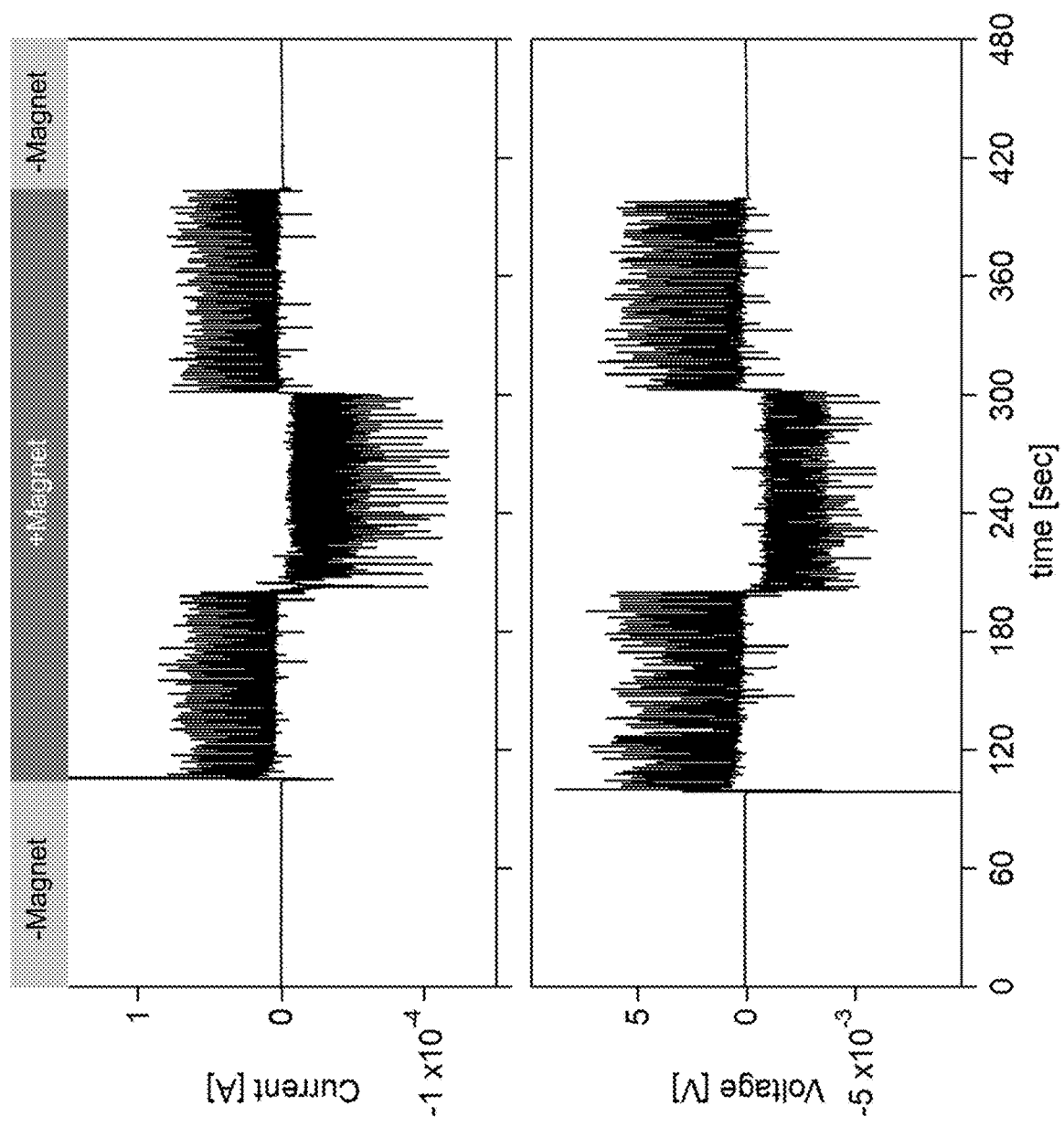
FIG. 26. Current (top) and voltage (bottom) measured without and with magnet in direct contact with the bottom, top, and again bottom portion of a nickel nanolayer during waveaction.

Nanolayers prepared from nickel, iron, and chromium were exposed to wave action while they were in contact with commercially available permanent magnets having surface flux densities of up to 6400 Gauss. Bracket-shaped magnets were used, having up to 0.64 Tesla at each pointed end and around 0.05 T in the center (FIG. 24). Wave action at approximately 0.5 Hz with a wave height velocity of 5 cm sec$^{-1}$ led to an increase in peak-to-peak current from around 1 microA without the magnet (FIG. 25A) to 50 μA when the magnet was present (FIG. 25B). The voltage increased from around 50 μV to around 5 mV. These results indicate that the difference in maximum peak power is 100 μW (resp. 100 nW) with (resp. without) the metal nanolayer per wave event for the wetted area of 2.5×5 cm$^2$ at the wave height velocity (5 cm s$^{-1}$) and wave frequency (0.5 Hz) of the wavetank. Additional experiments showed that controlling how the magnet contacts the metal nanolayer can be used to control the signage of the output voltage and current (FIG. 26). When the top pointed end of the magnet touched the top insulation of the nanolayer, the recorded current and voltage were positive, whereas the sign changed when moving the magnet down so that the bottom pointed end of the magnet touched the bottom insulation of the nanolayer. The sign change was seemingly instantaneous, without memory effects. Placing the magnet with both pointed ends to be in contact with the nanolayer (not the insulation) generated a somewhat smaller negative current. Removing the magnet resulted in a several-minute-long return to the original baseline performance.

Controls using two glass slides without any metal nanolayers, wired up like the ones coated with the metal nanolayers, showed current densities of ~5 nA and voltages around 5 mV during wave action without the magnet, which increased to ~100 nA and ~50 mV when the magnet was present. Additional controls using a piece of copper tape or the magnet itself, wired up like the metal nanolayers, showed no to negligible change in current or voltage with wave action, whether the magnet was present or not. Covering the magnet-facing nanolayer with Kapton tape of a few tens of μm thickness while leaving the tank-facing uncovered resulted in some minor magnetic enhancement of the current, indicating the former did most of the work in these experiments. Finally, a [-shaped magnet having pointed ends with a 0.62 T flux density but 6.3 mm×6.3 mm contact footprint yielded a peak current of 15 μA, about three times smaller than the 50 μA obtained from the magnet with the 6.3 mm×2.5 cm contact footprint, indicating the magnet: nanolayer contact area is important.

Figure 27:
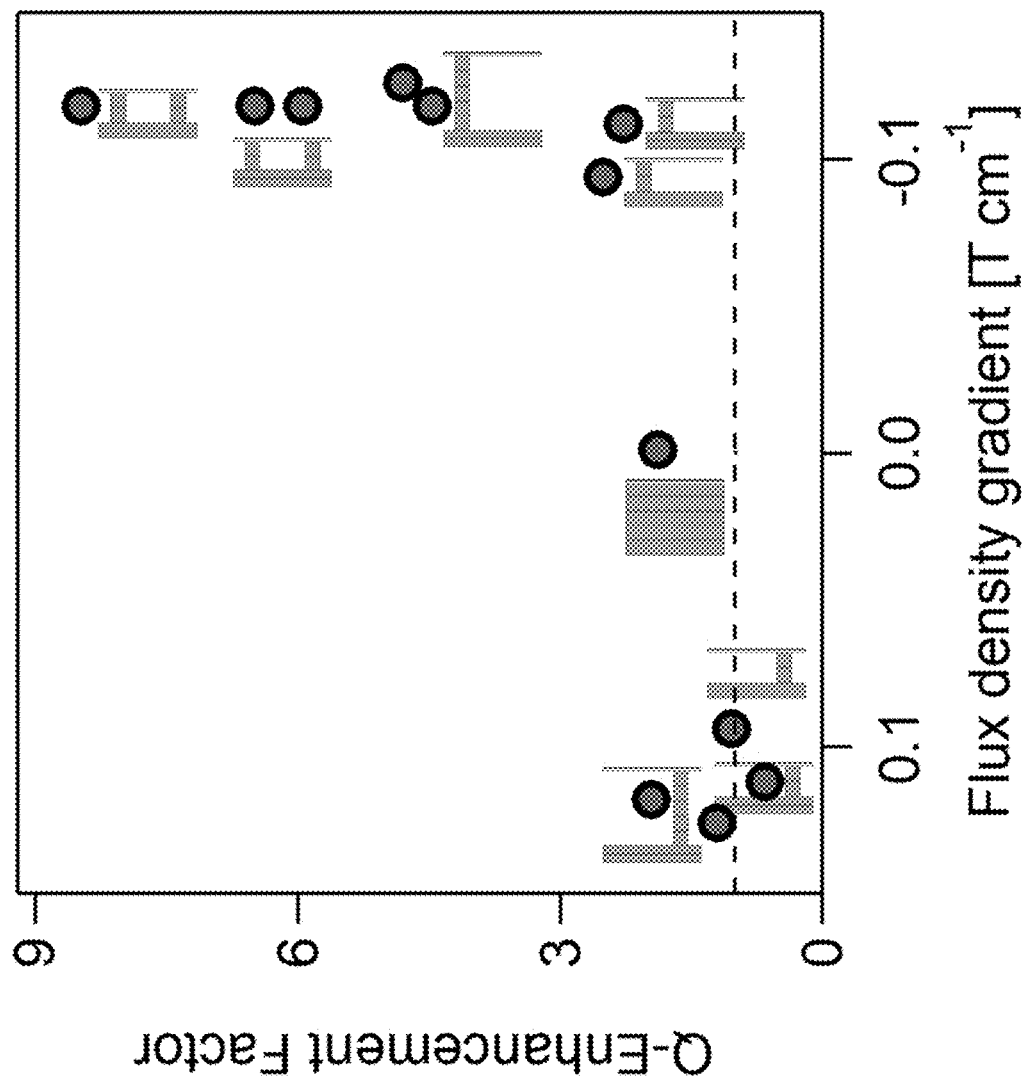
FIG. 27. Charge enhancement factor obtained for magnets exhibiting a maximum flux density of at least 0.59 T as a function of flux density gradient obtained for magnet assemblies having various shapes.

The current enhancement was then determined by the metal nanolayers as a function of magnetic flux density and magnet shape. To do so, a single glass slide, coated on one side with 10 nm nickel or iron, was employed, and a magnet of a given shape, assembled using 6.35 mm and 12.7 mm thick magnets of 5 cm width and varying length, was brought in contact with the glass side. The magnetic flux density was attenuated by ~10 percent by the glass slide. The current was collected and rectified, and it was integrated over 50 seconds to compute the total charge moving during 25 successive wave events. The charge (Q) enhancement was then computed as the ratio of the charge obtained for 25 wave events in the presence and absence of a given magnet. FIG. 27 shows Q-enhancements of close to nine were observed for [-stacks, while Γ-stacks led to approximately five-fold Q-enhancement when flux density gradients approached+0.12 T cm$^{-1}$. Gradients of zero, or negatively signed gradients, resulted in less or no enhancement in charge. A second group of magnet stacks exhibiting 0.1 to 0.5 T maximum flux density resulted in more modest Q-enhancements, or none.

Taken together, it was found that [-shaped permanent magnets having flux densities of around 0.6 T that were in direct contact with 10 nm thin nickel and iron nanolayers amplified the current and voltage by a factor of about 100. The maximum possible peak power from metal nanolayer-free glass slides also increased by a factor of ~50 from ~5 nW per wave event to ~0.25 µW per wave event at the same wetted area of 10 nm nickel. The effect was possible because of the several hundred Ohm resistance exhibited by the metal nanolayers, which, in contrast to insulating materials such as glass, allowed for a considerable current to flow while a modest voltage was maintained. Magnetic fields from molecular magnets have been reported for harvesting energy at acoustic and ultrasound frequencies, used in ferroic materials via magnetistriction to convert mechanical deformations into electricity, and employed in rotating induction magnets driven by flowing water.

The approach presented here requires no moving parts and emits zero noise, uses inexpensive permanent magnets in various geometries, and employs nanolayers that are prepared from inexpensive elements in a single step. Besides a steep flux density gradient, the magnetic enhancement observed also utilizes flux densities of several thousand Gauss. Nanolayers can be prepared from metals having strong magnetic susceptibilities (nickel and iron). The magnetic susceptibility of the oxides that spontaneously form on their surfaces may also be important as experiments carried out on liquid drops and in flow cells suggest a role for intra-oxide electron transfer (or polaron mobility) for Fe, V, and Ni nanolayers whose thermal oxides contain several metal oxidation states. Charge carrier motion involving donor-acceptor chemistry between Fe(II) and Fe(III) in the oxide nano-overlayer of iron, or Ni(II)/Ni(III) in Ni, provides a conduit for electron mobility through the oxide, similar to conduction through bulk oxides of Fe. In the oxide nano-overlayer, the magnetic field can align the spins of the metal cations ($Ni^{2+}/Ni^{3+}$ and $Fe^{2+}/Fe^{3+}$)[1] which, in turn, can lower the energy difference for charge to hop between two sites as the polarons in the oxide nano-overlayer move along with the upwards and downwards motion of the wave. Magnetoresistance is unlikely to be important, given that $(\mu_o B)^2$ at 1 T is in the $10^{-4}$ to $10^{-2}$ range for metals and their oxides.

One gram of standard purity metal (Ni, Fe, V, etc) consists of $1 \times 10^{22}$ Ni atoms. These cover a 3.35 m×3.35 m area to a height of 10 nm. The performance values in the Instant Ocean wavetank (~2 s wave period, 50 µA and 5 mV for 10 nm Ni at 5 cm $sec^{-1}$ wave height velocity when the [-shaped magnet is in contact with out 2.5×5 $cm^2$ wetted nanolayer area) indicate such an area can produce around 400 milliA peak currents with each wave event, or ~20 kA per day, at ~5 mV peak voltage, in the wavetank. For gentle to moderate breezes, average deep-water wave amplitudes were 1-2 m, with ~6 sec periods. The velocity at which the wave then moved along the metal nanolayer was ~30 cm $s^{-1}$, or ~6× the wave height velocity in the wavetank. The demonstrated linear dependence of current output on flow velocity[1] (1 to 3 microA $cm^{-2}$ for each cm $s^{-1}$ increase in flow velocity) means that one can expect more current under such conditions in the field. Given the devices operate in series and parallel, opportunities exist to design high total internal surface area structures accessible to metal pulsed vapor deposition (PVD), such as accordion or honeycomb structures, having footprints commensurate with open ocean operation.

Materials and Methods.

The nanolayers were prepared as described in the previous examples, with one modification: here, a PVD deposition system (HHV ATS500 laboratory coater) operating at a base pressure of $\sim 10^{-7}$ to $10^{-6}$ mbar was used. Standard purity metal sources were obtained from Kurt J. Lesker and handled as described in the previous examples. A Tetra wavetank was used; it was filled to about half with City of Evanston tap water, and the recommended amount of Instant Ocean Sea Salt mix was added. Wave action was established using a programmable wireless quiet drive smart wave maker (Ecotech Marine MP40W QD). Water was exchanged approximately every month and a half, during which algae growth or biofilm formation on the inside of the tank was not observable by eye. Once deposited on standard glass microscope slides (VWR), the metal nanolayers were wired up using conducting copper tape with conductive adhesive (Freely, Inc.), ethernet-grade wire was pressed onto the copper tape and sandwiched using one more layer of copper tape, and the electrical contacts were insulated using Temflex 1700 electrical tape (3M). Current, voltage, and resistance measurements were performed using Keithley instrumentation (6485 ammeter and 2100 voltmeter) interfaced with a workstation running a custom-written Mathematica (Wolfram) program for a 10 Hz data logging rate. Magnets (N52 grade) were obtained from K&J magnetics as well as DIYMAG in the various shapes and sizes needed to map out the field gradient effect described in the main text. The magnets were sealed in a Ni:Cr:Ni sheath of a few hundred µm in thickness. Flux densities were mapped out using an MF-30K AC/DC Gauss meter (Latnex) clamped onto a Thorlabs x-y micrometer stage.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A liquid flow-based device comprising:
 a metal layer comprising a metal;
 an amphoteric metal oxide film adjacent to the metal layer at an interface, the amphoteric metal oxide film having a surface disposed opposite the interface, wherein the metal layer has a thickness that facilitates charge carrier motion parallel to the interface; and
 at least one of: an electronic device that consumes electrical power connected laterally across the metal layer and configured to be powered by a current running parallel to the interface; an energy storage device connected laterally across the metal layer and configured to be charged by a current running parallel to the interface; a voltage measuring device configured to measure a voltage across the metal layer; and a current measuring device connected laterally across the metal layer and configured to measure a current running parallel to the interface.

2. The device of claim 1, wherein the metal layer is disposed on a support comprising a magnet and the metal has magnetic susceptibility.

3. The device of claim 1, wherein the amphoteric metal oxide film comprises metal oxide dendrites.

4. The device of claim 1, wherein the metal layer is an iron layer, and the amphoteric metal oxide film is an iron oxide film.

5. The device of claim 1, wherein the metal layer is an aluminum layer, and the amphoteric metal oxide film is an aluminum oxide film.

6. The device of claim 1, wherein the metal layer is a zinc layer, and the amphoteric metal oxide film is a zinc oxide film.

7. The device of claim 1, wherein the metal layer is a nickel layer, and the amphoteric metal oxide film is a nickel oxide film.

8. The device of claim 1, wherein the metal substrate has a thickness of no greater than 50 nm.

9. The device of claim 8, wherein the amphoteric metal oxide film has a thickness of no greater than 10 nm.

10. The device of claim 1, wherein the electronic device that consumes electrical power is connected laterally across the metal layer.

11. The device of claim 1, wherein the energy storage device is connected laterally across the metal layer.

12. The device of claim 1, wherein the voltage measuring device or the current measuring device is connected laterally across the metal layer.

13. A method of harvesting energy using a liquid flow-based device comprising:
a metal layer comprising a metal;
an amphoteric metal oxide film adjacent to the metal layer at an interface, the amphoteric metal oxide film having a surface disposed opposite the interface, wherein the metal layer has a thickness that facilitates charge carrier motion parallel to the interface; and
at least one of: an electronic device that consumes electrical power connected laterally across the metal layer and configured to be powered by a current running parallel to the interface; an energy storage device connected laterally across the metal layer and configured to be charged by a current running parallel to the interface; a voltage measuring device configured to measure a voltage across the metal layer; and a current measuring device connected laterally across the metal layer and configured to measure a current running parallel to the interface, the method comprising:
exposing the surface of the amphoteric metal oxide film to an intermittent flow of an ionic solution or to a flow of an ionic solution having a temporally varying ionic conductivity, wherein the intermittent flow or the temporally varying ionic conductivity generates a current in the metal layer; and
powering the electronic device or charging the energy storage device with the generated current.

14. The method of claim 13, wherein the metal layer is disposed on a support comprising a magnet, and the metal has magnetic susceptibility, and further wherein the surface of the amphoteric metal oxide film is exposed to the intermittent flow of the ionic solution or to the flow of the ionic solution having a temporally varying ionic conductivity in the presence of a magnetic field produced by the magnet.

15. The method of claim 13, wherein the ionic solution is an aqueous salt solution.

16. The method of claim 13, wherein the flow of the ionic solution is intermittent.

17. The method of claim 16, wherein the intermittent flow comprises discrete droplets of the ionic solution.

18. The method of claim 16, wherein the intermittent flow comprises waves of the ionic solution.

19. The method of claim 13, wherein the flow of the ionic solution has a temporally varying ionic conductivity.

20. The method of claim 19, wherein the flow of the ionic solution is provided by a liquid stream comprising sections of a first ionic solution having a first ionic conductivity alternating with sections of a second ionic solution having a lower ionic conductivity than the first ionic solution.

21. The method of claim 13, wherein the ionic solution comprises salinized water from a natural body of water.

22. A method of monitoring the flow of an ionic solution using a liquid flow-based device comprising:
a metal layer comprising a metal;
an amphoteric metal oxide film adjacent to the metal layer at an interface, the amphoteric metal oxide film having a surface disposed opposite the interface, wherein the metal layer has a thickness that facilitates charge carrier motion parallel to the interface; and
at least one of: an electronic device that consumes electrical power connected laterally across the metal layer and configured to be powered by a current running parallel to the interface; an energy storage device connected laterally across the metal layer and configured to be charged by a current running parallel to the interface; a voltage measuring device configured to measure a voltage across the metal layer; and a current measuring device connected laterally across the metal layer and configured to measure a current running parallel to the interface, the method comprising:
exposing the surface of the amphoteric metal oxide film to an intermittent flow of an ionic solution or to a flow of an ionic solution having a temporally varying ionic conductivity, wherein the intermittent flow or the temporally varying ionic conductivity generates a current in the metal layer; and
measuring the voltage across the metal layer as the ionic solution passes over the surface of the amphoteric metal oxide film.

23. The method of claim 22, wherein the metal layer is disposed on a support comprising a magnet, and the metal has magnetic susceptibility, and further wherein the surface of the amphoteric metal oxide film is exposed to the intermittent flow of the ionic solution or to the flow of the ionic solution having a temporally varying ionic conductivity in the presence of a magnetic field produced by the magnet.

24. The method of claim 22, wherein the ionic solution is an aqueous salt solution.

25. The method of claim 22, wherein the flow of the ionic solution is intermittent.

26. The method of claim 22, wherein the flow of the ionic solution has a temporally varying ionic conductivity.

* * * * *